US010017823B2

(12) United States Patent
Park et al.

(10) Patent No.: US 10,017,823 B2
(45) Date of Patent: Jul. 10, 2018

(54) ANALYTICAL METHOD FOR INCREASING SUSCEPTIBILITY OF MOLECULAR TARGETED THERAPY IN HEPATOCELLULAR CARCINOMA

(71) Applicant: CBS BIOSCIENCE, CO., LTD, Daejeon (KR)

(72) Inventors: Jin-Young Park, Seoul (KR); Young-Ho Moon, Daejeon (KR); Jung-Hee Kwon, Daejeon (KR)

(73) Assignee: CBS BIOSCIENCE, CO., LTD, Daejeon (KR)

(*) Notice: Subject to any disclaimer, the term of this patent is extended or adjusted under 35 U.S.C. 154(b) by 52 days.

(21) Appl. No.: 14/765,304

(22) PCT Filed: Apr. 16, 2014

(86) PCT No.: PCT/KR2014/003281
§ 371 (c)(1),
(2) Date: Jul. 31, 2015

(87) PCT Pub. No.: WO2014/175593
PCT Pub. Date: Oct. 30, 2014

(65) Prior Publication Data

US 2015/0376715 A1 Dec. 31, 2015

(30) Foreign Application Priority Data

Apr. 25, 2013 (KR) ........................ 10-2013-0046279

(51) Int. Cl.
*C12Q 1/68* (2018.01)
*C12Q 1/6886* (2018.01)

(52) U.S. Cl.
CPC ..... *C12Q 1/6886* (2013.01); *C12Q 2600/106* (2013.01); *C12Q 2600/158* (2013.01)

(58) Field of Classification Search
None
See application file for complete search history.

(56) References Cited

U.S. PATENT DOCUMENTS

2007/0037224 A1 2/2007 Hamer et al.
2008/0311604 A1 12/2008 Elting et al.
2010/0233680 A1* 9/2010 Taylor .................. C12Q 1/6886 435/6.14
2010/0234381 A1 9/2010 Parada et al.
2011/0257035 A1 10/2011 Pena
2013/0012550 A1 1/2013 Wilhelm

OTHER PUBLICATIONS

Definition of “Measuring” in The Free Dictionary by Farlex. Available via url: <.thefreedictionary.com/measuring> printed on Jul. 31, 2017.*
Kwon et al PLoS ONE. Jun. 13, 2013. 8(6): e64260.*
Zhang et al (Clinical Genitourinary Cancer. Published online Oct. 9, 2012.11(2): 134-140.*
Chung et al Cancer Letters. 2005. 217: 231-236.*
Abou-Alfa et al., “Phase II Study of Sorafenib in Patients With Advanced Hepatocellular Carcinoma”, Journal of Clinical Oncology, vol. 24, No. 26, pp. 4293-4300, Sep. 10, 2006.
Tai et al., “Signal transducer and activator of transcription 3 is a major kinase-independent target of sorafenib in hepatocellular carcinoma”, Journal of Hepatology, vol. 55, pp. 1041-1048, (2011).
Wilhelm et al., “Preclinical overview of sorafenib, a multikinase inhibitor that targets both Raf and VEGF and PDGF receptor tyrosine kinase signaling”, Mol Cancer Ther, vol. 7, pp. 3129-3140, (2008).
Yang et al., “Hepatocellular carcinoma: a global view”, Nat Rev Gastroenterol Hepatol., vol. 7, No. 8, pp. 448-458, (2010).
Villanueva et al., “Targeted Therapies for Hepatocellular Carcinoma”, Gastroenterology, vol. 140, pp. 1410-1426, (2011).
Llovet et al., “Sorafenib in Advanced Hepatocellular Carcinoma”, N Engl J Med, vol. 359, pp. 378-390, (2008).
Cheng et al., “Efficacy and safety of sorafenib in patients in the Asia-Pacific region with advanced hepatocellular carcinoma: a phase III randomised, double-blind, placebo-controlled trial”, Lancet Oncol, vol. 10, pp. 25-34, (2009).
Zhu, “Molecularly Targeted Therapy for Advanced Hepatocellular Carcinoma in 2012: Current Status and Future Perspectives”, Semin Oncol, vol. 39, pp. 493-502, (2012).
Huynh, “Molecularly targeted therapy in hepatocellular carcinoma”, Biochemical Pharmacology, vol. 80, pp. 550-560, (2010).
Villanueva et al., “Second-Line Therapies in Hepatocellular Carcinoma: Emergence of Resistance to Sorafenib”, Clin Cancer Res, vol. 18, No. 7, pp. 1824-1826, (2012).
Vogel et al., “Efficacy and Safety of Trastuzumab as a Single Agent in First-Line Treatment of HER2-Overexpressing Metastatic Breast Cancer”, J Clin Oncol, vol. 20, pp. 719-726, (2002).
Lynch et al., “Activating Mutations in the Epidermal Growth Factor Receptor Underlying Responsiveness of Non-Small-Cell Lung Cancer to Gefitinib”, N Engl J Med, vol. 350, No. 21, pp. 2129-2139, (2004).
West et al., “A Novel Classification of Lung Cancer into Molecular Subtypes”, Plos ONE, vol. 7, Issue 2, e31906, 11 pages, (2012).

(Continued)

*Primary Examiner* — Carla J Myers
(74) *Attorney, Agent, or Firm* — Vorys, Sater, Seymour & Pease LLP; Mih Suhn Koh

(57) ABSTRACT

Provided herein is an analytical method for determining whether a hepatocellular carcinoma patient has susceptibility or resistance to sorafenib treatment by analyzing the mRNA expression of FGFR1, optionally along with the mRNA expressions of other biomarkers (i.e., VEGFR2, PDGFRβ, c-KIT, c-RAF, EGFR, and/or mTOR) to select a patient having susceptibility to sorafenib treatment and a patient having resistance to sorafenib treatment before employing molecular targeted therapy with sorafenib.

2 Claims, 10 Drawing Sheets

(56) References Cited

OTHER PUBLICATIONS

Vidwans et al., "A Melanoma Molecular Disease Model", Plos ONE, vol. 6, Issue 3, e18257, 10 pages, (2011).

Forner et al., "Current Strategy for Staging and Treatment: The BCLC Update and Future Prospects", Semin Liver Dis, vol. 30, pp. 61-74, (2010).

Edmondson et al., "Primary Carcinoma of the Liver: A Study of 100 Cases among 48,900 Necropsies", Cancer, vol. 7, No. 3, pp. 462-503, (1954).

* cited by examiner

[Fig. 1]
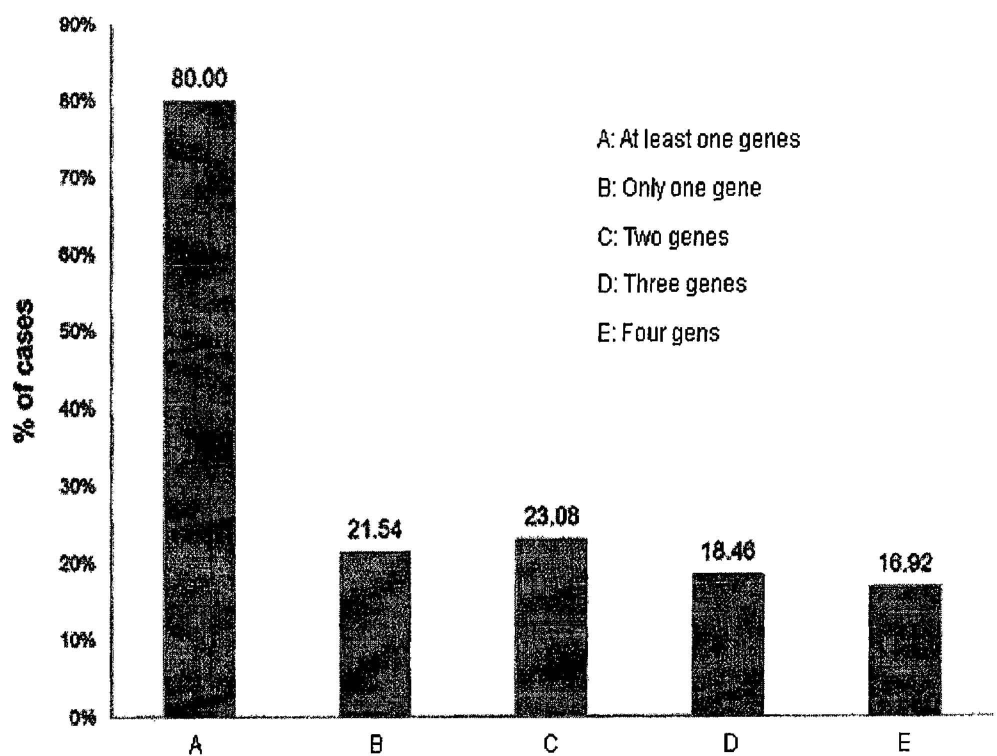

[Fig. 2a]
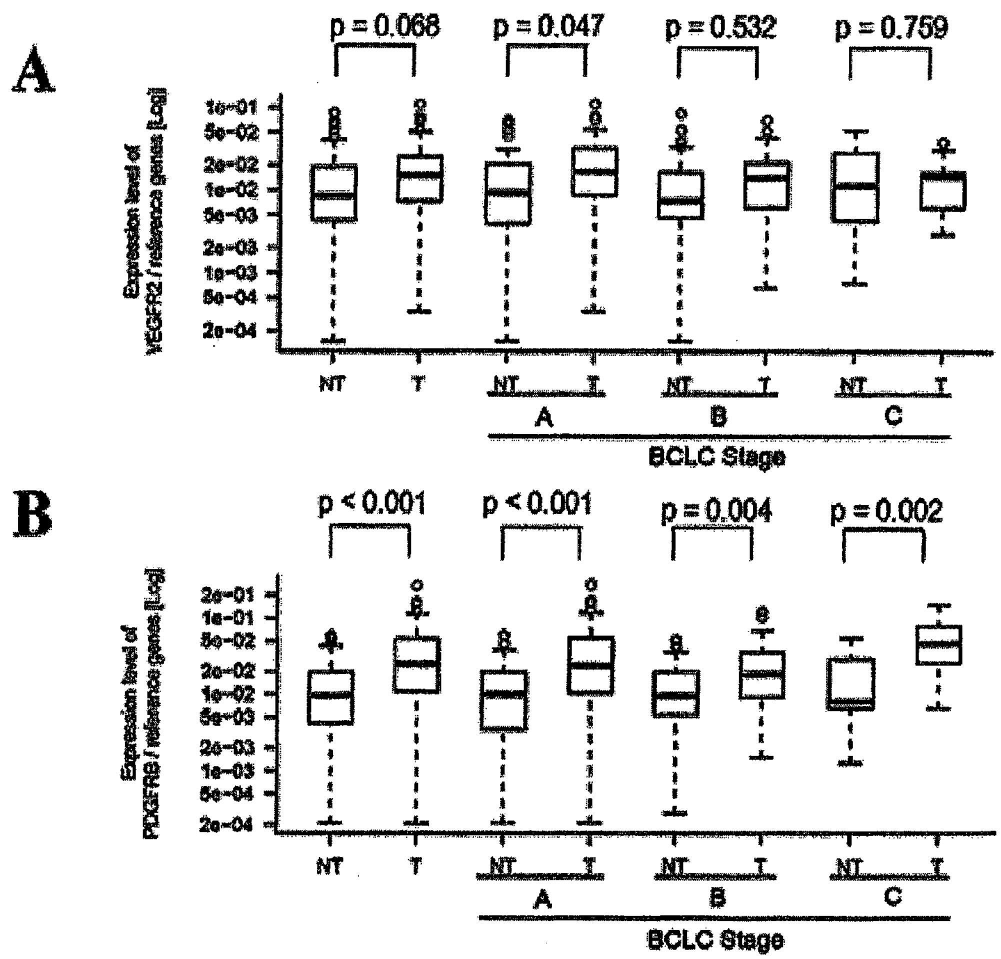

[Fig. 2b]
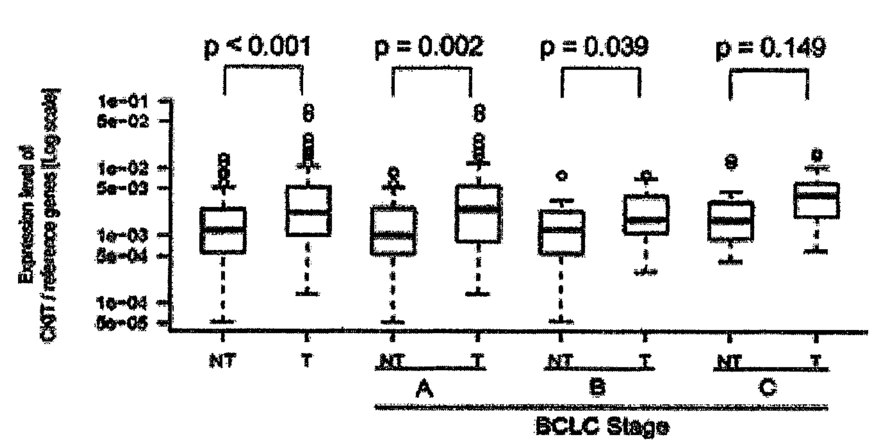
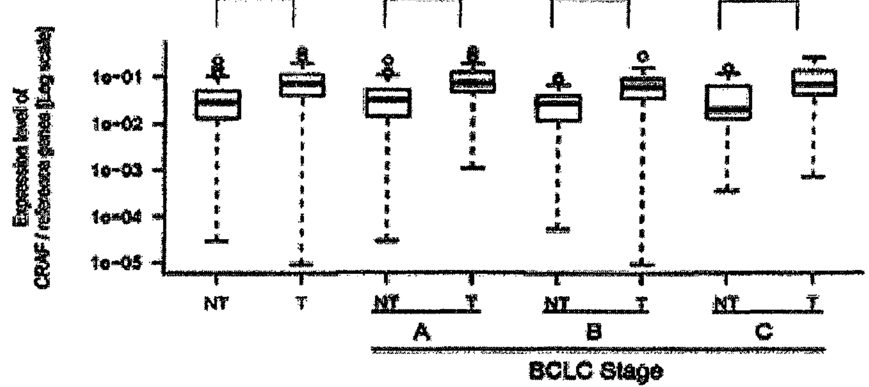

[Fig. 2c]
E
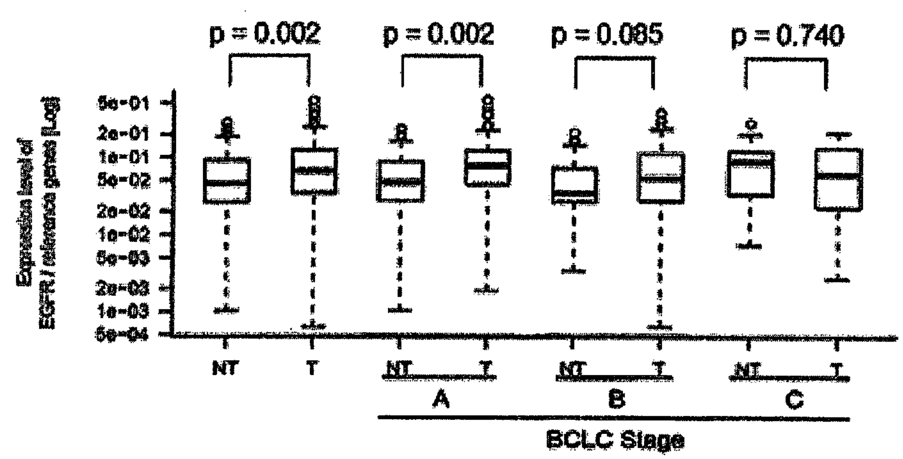
F
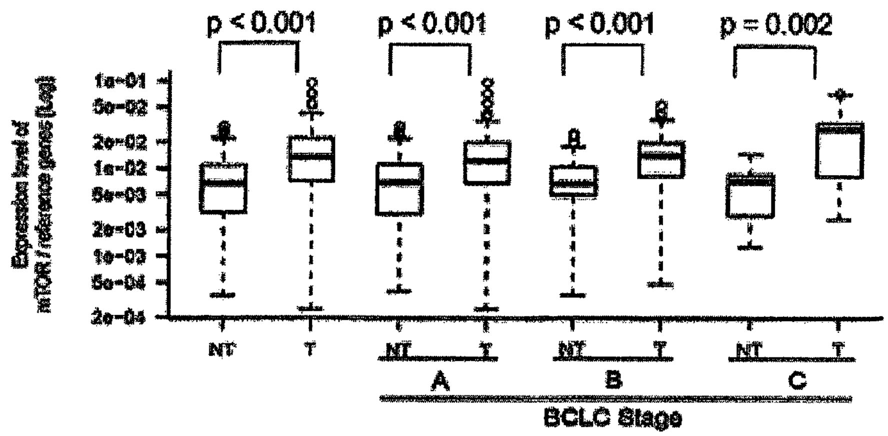

[Fig. 2d]
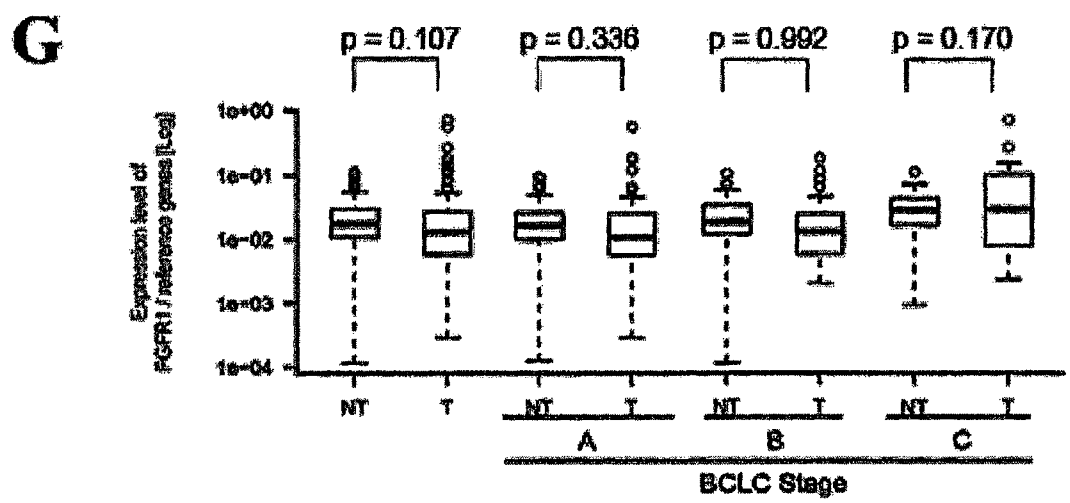

[Fig. 3]
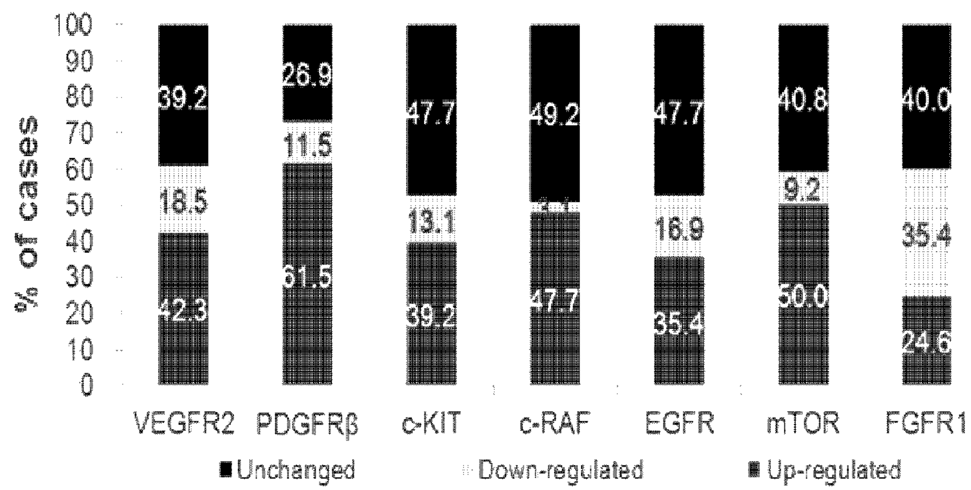
[Fig. 4a]
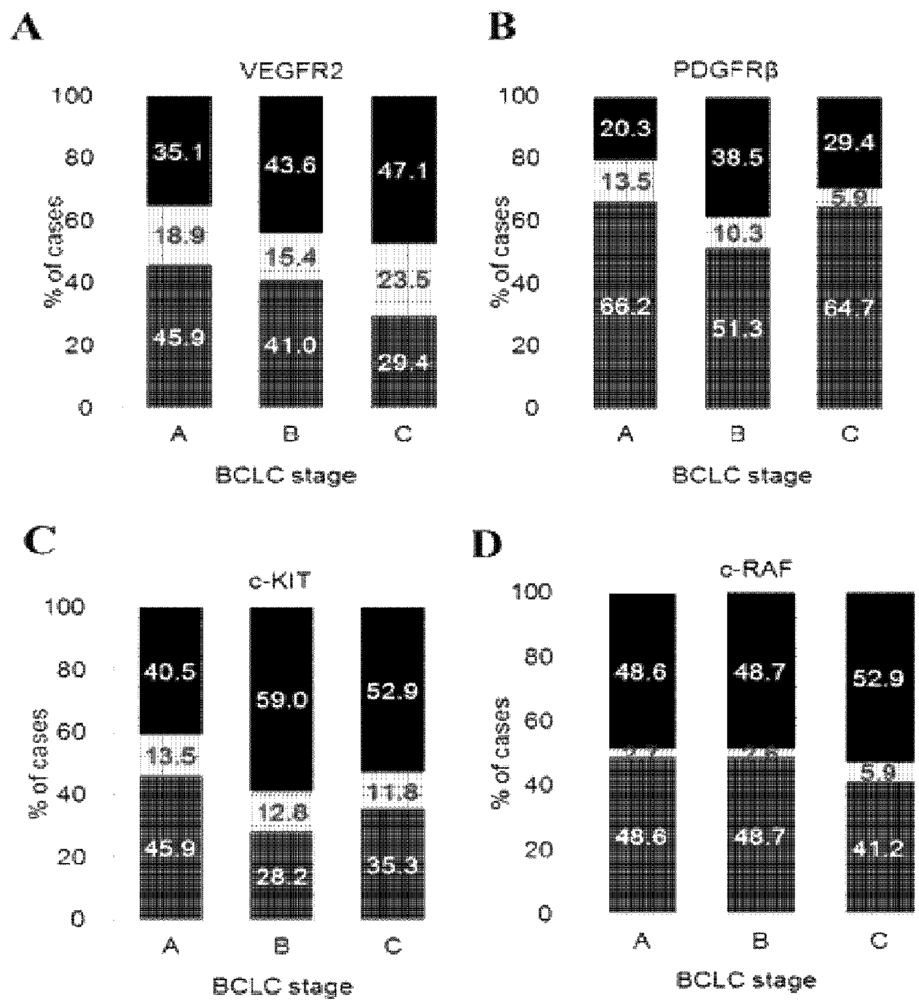

[Fig. 4b]
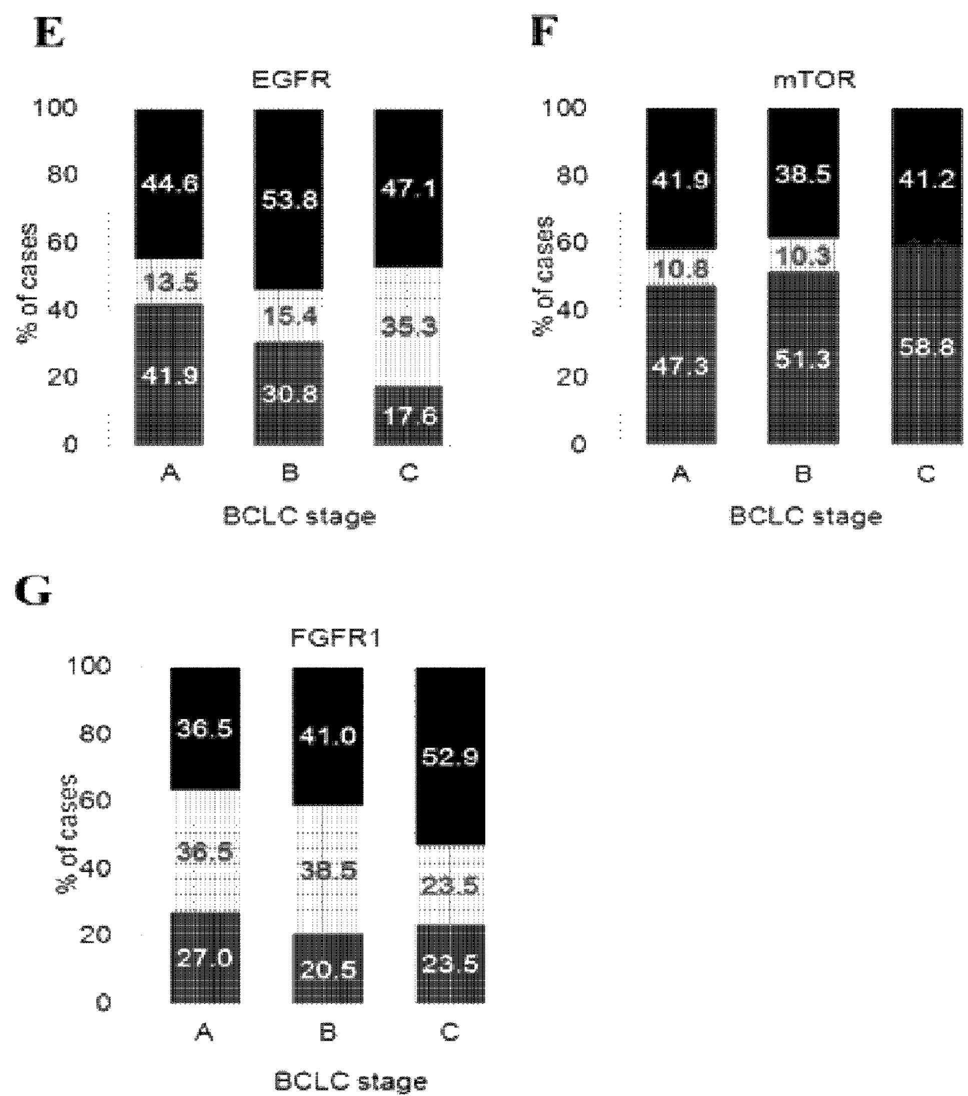

[Fig. 5]
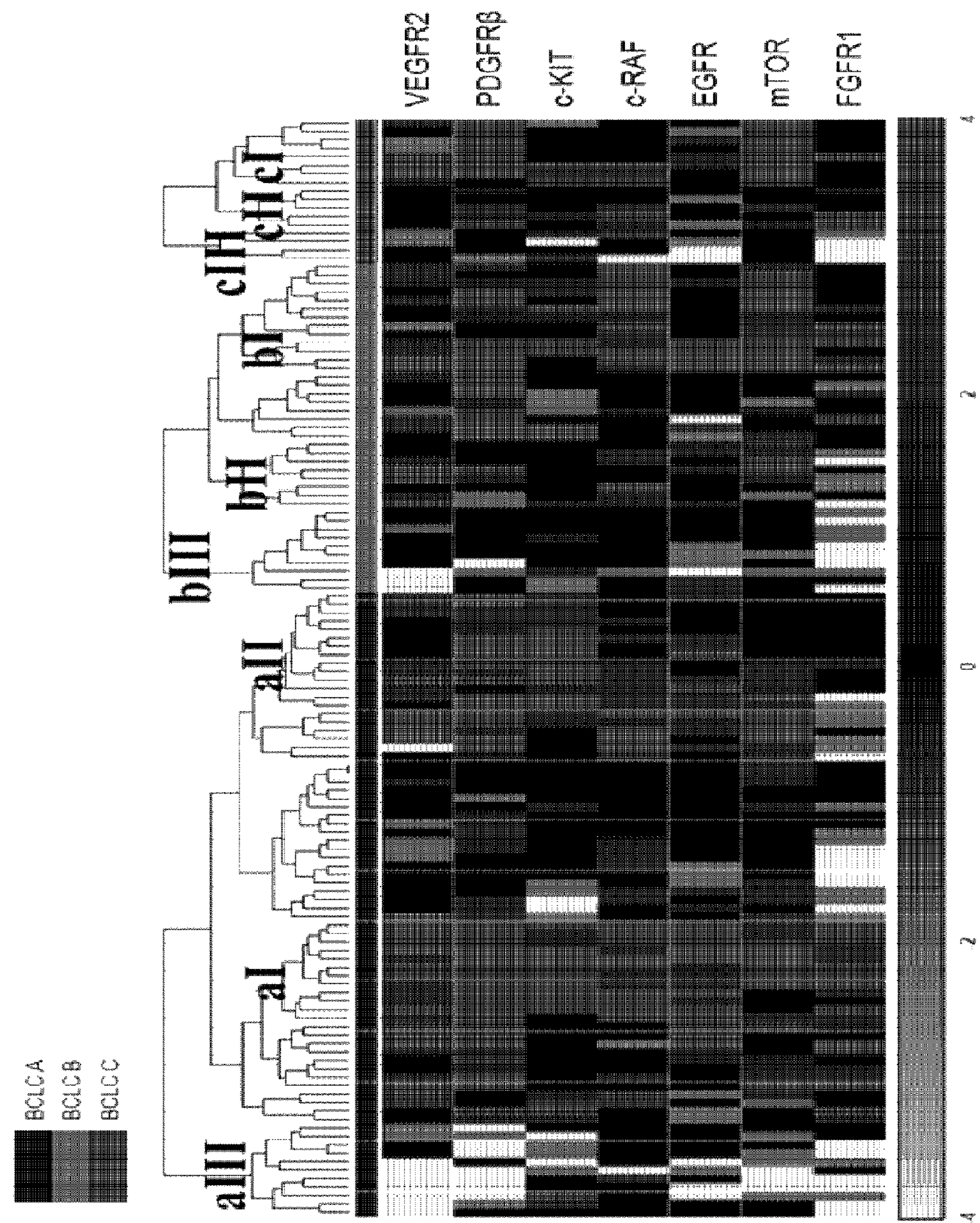

[Fig. 6]
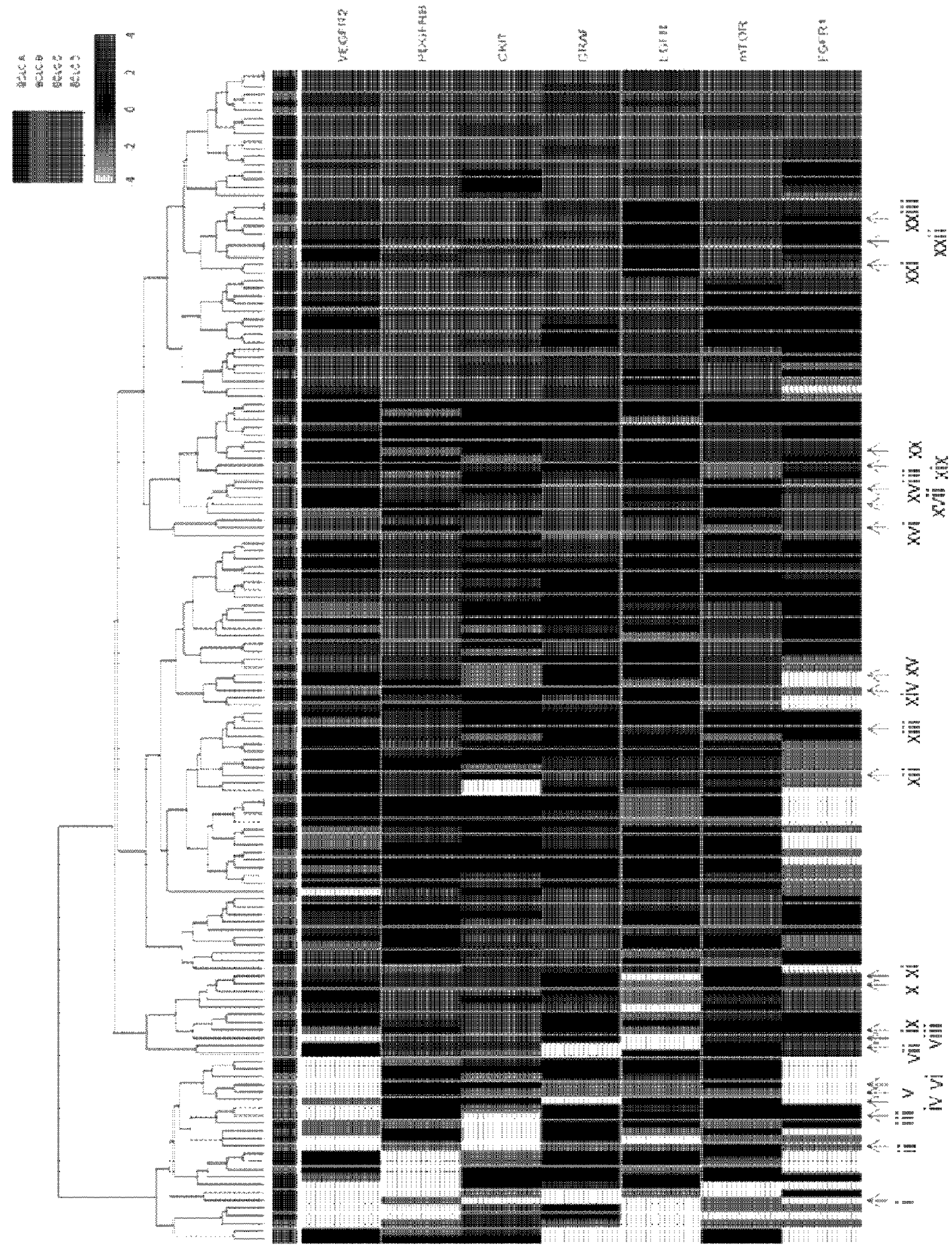

[Fig. 7]
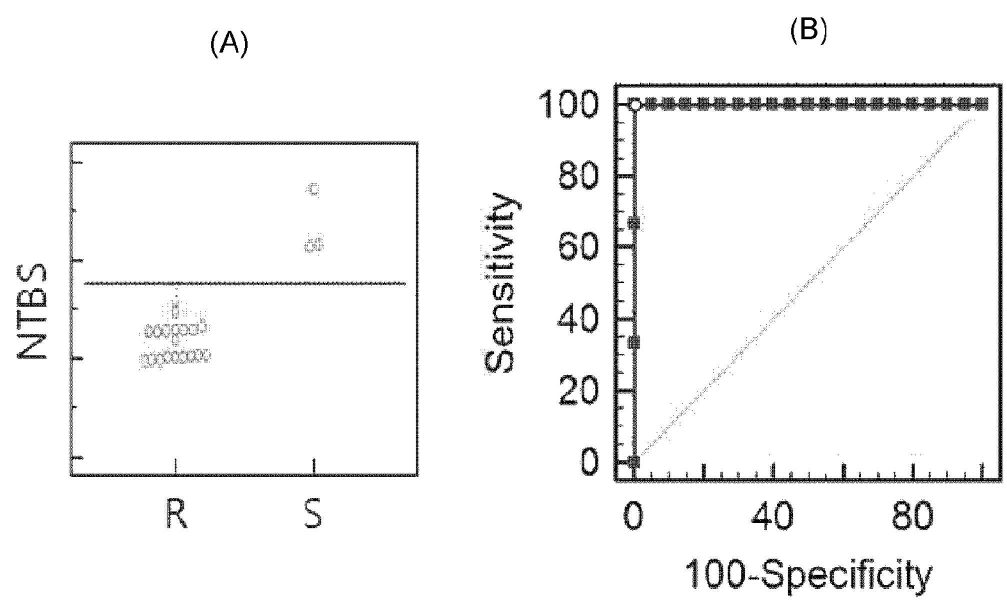

SEQUENCE LISTING

```
<160> NUMBER OF SEQ ID NOS: 43

<210> SEQ ID NO 1
<211> LENGTH: 5895
<212> TYPE: DNA
<213> ORGANISM: homo sapiens

<400> SEQUENCE: 1

agatgcaggg gcgcaaacgc caaaggagac caggctgtag gaagagaagg gcagagcgcc      60

ggacagctcg gcccgctccc cgtcctttgg ggccgcggct ggggaactac aaggcccagc     120

aggcagctgc agggggcgga ggcggaggag ggaccagcgc gggtgggagt gagagagcga     180

gccctcgcgc cccgccggcg catagcgctc ggagcgctct tgcggccaca ggcgcggcgt     240

cctcggcggc gggcggcagc tagcgggagc cgggacgccg gtgcagccgc agcgcgcgga     300

ggaacccggg tgtgccggga gctgggcggc cacgtccgga cgggaccgag acccctcgta     360

gcgcattgcg gcgacctcgc cttccccggc cgcgagcgcg ccgctgcttg aaaagccgcg     420

gaacccaagg acttttctcc ggtccgagct cggggcgccc cgcagggcgc acggtacccg     480

tgctgcagtc gggcacgccg cggcgccggg gcctccgcag ggcgatggag cccggtctgc     540

aaggaaagtg aggcgccgcc gctgcgttct ggaggagggg ggcacaaggt ctggagaccc     600

cgggtggcgg acgggagccc tccccccgcc ccgcctccgg ggcaccagct ccggctccat     660

tgttcccgcc cgggctggag gcgccgagca ccgagcgccg ccgggagtcg agcgccggcc     720

gcggagctct tgcgaccccg ccaggacccg aacagagccc gggggcggcg ggccggagcc     780

ggggacgcgg gcacacgccc gctcgcacaa gccacggcgg actctcccga ggcggaacct     840

ccacgccgag cgagggtcag tttgaaaagg aggatcgagc tcactgtgga gtatccatgg     900

agatgtggag ccttgtcacc aacctctaac tgcagaactg ggatgtggag ctggaagtgc     960

ctcctcttct gggctgtgct ggtcacagcc acactctgca ccgctaggcc gtccccgacc    1020

ttgcctgaac aagcccagcc ctggggagcc cctgtggaag tggagtcctt cctggtccac    1080

cccggtgacc tgctgcagct tcgctgtcgg ctgcgggacg atgtgcagag catcaactgg    1140

ctgcgggacg gggtgcagct ggcggaaagc aaccgcaccc gcatcacagg ggaggaggtg    1200

gaggtgcagg actccgtgcc cgcagactcc ggcctctatg cttgcgtaac cagcagcccc    1260

tcgggcagtg acaccaccta cttctccgtc aatgtttcag atgctctccc ctcctcggag    1320

gatgatgatg atgatgatga ctcctcttca gaggagaaag aaacagataa caccaaacca    1380

aaccgtatgc ccgtagctcc atattggaca tccccagaaa agatggaaaa gaaattgcat    1440

gcagtgccgg ctgccaagac agtgaagttc aaatgccctt ccagtgggac cccaaacccc    1500

acactgcgct ggttgaaaaa tggcaaagaa ttcaaacctg accacagaat tggaggctac    1560

aaggtccgtt atgccacctg gagcatcata atggactctg tggtgccctc tgacaagggc    1620
```

-continued

```
aactacacct gcattgtgga gaatgagtac ggcagcatca accacacata ccagctggat   1680
gtcgtggagc ggtcccctca ccggcccatc ctgcaagcag ggttgcccgc caacaaaaca   1740
gtggccctgg gtagcaacgt ggagttcatg tgtaaggtgt acagtgaccc gcagccgcac   1800
atccagtggc taaagcacat cgaggtgaat gggagcaaga ttggcccaga caacctgcct   1860
tatgtccaga tcttgaagac tgctggagtt aataccaccg acaaagagat ggaggtgctt   1920
cacttaagaa atgtctcctt tgaggacgca ggggagtata cgtgcttggc gggtaactct   1980
atcggactct cccatcactc tgcatggttg accgttctgg aagccctgga agagaggccg   2040
gcagtgatga cctcgcccct gtacctggag atcatcatct attgcacagg ggccttcctc   2100
atctcctgca tggtggggtc ggtcatcgtc tacaagatga agagtggtac caagaagagt   2160
gacttccaca gccagatggc tgtgcacaag ctggccaaga gcatccctct gcgcagacag   2220
gtgtctgctg actccagtgc atccatgaac tctggggttc ttctggttcg gccatcacgg   2280
ctctcctcca gtgggactcc catgctagca ggggtctctg agtatgagct tcccgaagac   2340
cctcgctggg agctgcctcg ggacagactg gtcttaggca aacccctggg agagggctgc   2400
tttgggcagg tggtgttggc agaggctatc gggctggaca aggacaaacc caaccgtgtg   2460
accaaagtgg ctgtgaagat gttgaagtcg gacgcaacag agaaagactt gtcagacctg   2520
atctcagaaa tggagatgat gaagatgatc gggaagcata agaatatcat caacctgctg   2580
ggggcctgca cgcaggatgg tcccttgtat gtcatcgtgg agtatgcctc caagggcaac   2640
ctgcgggagt acctgcaggc ccggaggccc ccagggctgg aatactgcta caaccccagc   2700
cacaacccag aggagcagct ctcctccaag gacctggtgt cctgcgccta ccaggtggcc   2760
cgaggcatgg agtatctggc ctccaagaag tgcatacacc gagacctggc agccaggaat   2820
gtcctggtga cagaggacaa tgtgatgaag atagcagact ttggcctcgc acgggacatt   2880
caccacatcg actactataa aaagacaacc aacggccgac tgcctgtgaa gtggatggca   2940
cccgaggcat tatttgaccg gatctacacc caccagagtg atgtgtggtc tttcggggtg   3000
ctcctgtggg agatcttcac tctgggcggc tccccatacc ccggtgtgcc tgtggaggaa   3060
cttttcaagc tgctgaagga gggtcaccgc atggacaagc ccagtaactg caccaacgag   3120
ctgtacatga tgatgcggga ctgctggcat gcagtgccct cacagagacc caccttcaag   3180
cagctggtgg aagacctgga ccgcatcgtg gccttgacct ccaaccagga gtacctggac   3240
ctgtccatgc ccctggacca gtactccccc agctttcccg acacccggag ctctacgtgc   3300
tcctcagggg aggattccgt cttctctcat gagccgctgc ccgaggagcc ctgcctgccc   3360
cgacacccag cccagcttgc caatggcgga ctcaaacgcc gctgactgcc acccacacgc   3420
cctccccaga ctccaccgtc agctgtaacc ctcacccaca gcccctgctg ggcccaccac   3480
ctgtccgtcc ctgtcccctt tcctgctggc aggagccggc tgcctaccag gggccttcct   3540
gtgtggcctg ccttcacccc actcagctca cctctccctc cacctcctct ccacctgctg   3600
gtgagaggtg caaagaggca gatctttgct gccagccact tcatcccctc ccagatgttg   3660
gaccaacacc cctccctgcc accaggcact gcctggaggg cagggagtgg gagccaatga   3720
acaggcatgc aagtgagagc ttcctgagct ttctcctgtc ggtttggtct gttttgcctt   3780
cacccataag cccctcgcac tctggtggca ggtgccttgt cctcagggct acagcagtag   3840
ggaggtcagt gcttcgtgcc tcgattgaag gtgacctctg ccccagatag gtggtgccag   3900
tggcttatta attccgatac tagtttgctt tgctgaccaa atgcctggta ccagaggatg   3960
gtgaggcgaa ggccaggttg gggcagtgt  tgtggccctg gggcccagcc ccaaactggg   4020
```

```
ggctctgtat atagctatga agaaaacaca aagtgtataa atctgagtat atatttacat   4080
gtctttttaa aagggtcgtt accagagatt tacccatcgg gtaagatgct cctggtggct   4140
gggaggcatc agttgctata tattaaaaac aaaaaagaaa aaaaaggaaa atgtttttaa   4200
aaaggtcata tattttttgc tacttttgct gttttatttt tttaaattat gttctaaacc   4260
tattttcagt ttaggtccct caataaaaat tgctgctgct tcatttatct atgggctgta   4320
tgaaaagggt gggaatgtcc actggaaaga agggacaccc acgggccctg gggctaggtc   4380
tgtcccgagg gcaccgcatg ctcccggcgc aggttccttg taacctcttc ttcctaggtc   4440
ctgcacccag acctcacgac gcacctcctg cctctccgct gcttttggaa agtcagaaaa   4500
agaagatgtc tgcttcgagg gcaggaaccc catccatgca gtagaggcgc tgggcagaga   4560
gtcaaggccc agcagccatc gaccatggat ggtttcctcc aaggaaaccg gtggggttgg   4620
gctggggagg gggcacctac ctaggaatag ccacggggta gagctacagt gattaagagg   4680
aaagcaaggg cgcggttgct cacgcctgta atcccagcac tttgggacac cgaggtgggc   4740
agatcacttc aggtcaggag tttgagacca gcctggccaa cttagtgaaa ccccatctct   4800
actaaaaatg caaaaattat ccaggcatgg tggcacacgc ctgtaatccc agctccacag   4860
gaggctgagg cagaatccct tgaagctggg aggcggaggt tgcagtgagc cgagattgcg   4920
ccattgcact ccagcctggg caacagagaa aacaaaaagg aaaacaaatg atgaaggtct   4980
gcagaaactg aaacccagac atgtgtctgc cccctctatg tgggcatggt tttgccagtg   5040
cttctaagtg caggagaaca tgtcacctga ggctagtttt gcattcaggt ccctggcttc   5100
gtttcttgtt ggtatgcctc cccagatcgt ccttcctgta tccatgtgac cagactgtat   5160
ttgttgggac tgtcgcagat cttggcttct tacagttctt cctgtccaaa ctccatcctg   5220
tccctcagga acgggggaa aattctccga atgtttttgg ttttttggct gcttggaatt    5280
tacttctgcc acctgctggt catcactgtc ctcactaagt ggattctggc tcccccgtac   5340
ctcatggctc aaactaccac tcctcagtcg ctatattaaa gcttatattt tgctggatta   5400
ctgctaaata caaaagaaag ttcaatatgt tttcatttct gtagggaaaa tgggattgct   5460
gctttaaatt tctgagctag ggattttttg gcagctgcag tgttggcgac tattgtaaaa   5520
ttctctttgt ttctctctgt aaatagcacc tgctaacatt acaatttgta tttatgttta   5580
aagaaggcat catttggtga acagaactag gaaatgaatt tttagctctt aaaagcattt   5640
gctttgagac cgcacaggag tgtctttcct tgtaaaacag tgatgataat ttctgccttg   5700
gccctacctt gaagcaatgt tgtgtgaagg gatgaagaat ctaaaagtct tcataagtcc   5760
ttgggagagg tgctagaaaa atataaggca ctatcataat tacagtgatg tccttgctgt   5820
tactactcaa atcacccaca aatttcccca aagactgcgc tagctgtcaa ataaaagaca   5880
gtgaaattga cctga                                                    5895
```

```
<210> SEQ ID NO 2
<211> LENGTH: 6055
<212> TYPE: DNA
<213> ORGANISM: homo sapiens

<400> SEQUENCE: 2

actgagtccc gggaccccgg gagagcggtc aatgtgtggt cgctgcgttt cctctgcctg     60
cgccgggcat cacttgcgcg ccgcagaaag tccgtctggc agcctggata tcctctccta    120
ccggcacccg cagacgcccc tgcagccgcg gtcggcgccc gggctcccta gccctgtgcg    180
```

-continued

```
ctcaactgtc ctgcgctgcg gggtgccgcg agttccacct ccgcgcctcc ttctctagac    240
aggcgctggg agaaagaacc ggctcccgag ttctgggcat ttcgcccggc tcgaggtgca    300
ggatgcagag caaggtgctg ctggccgtcg ccctgtggct ctgcgtggag acccgggccg    360
cctctgtggg tttgcctagt gtttctcttg atctgcccag gctcagcata caaaaagaca    420
tacttacaat taaggctaat acaactcttc aaattacttg caggggacag agggacttgg    480
actggctttg gcccaataat cagagtggca gtgagcaaag ggtggaggtg actgagtgca    540
gcgatggcct cttctgtaag acactcacaa ttccaaaagt gatcggaaat gacactggag    600
cctacaagtg cttctaccgg gaaactgact tggcctcggt catttatgtc tatgttcaag    660
attacagatc tccatttatt gcttctgtta gtgaccaaca tggagtcgtg tacattactg    720
agaacaaaaa caaaactgtg gtgattccat gtctcgggtc catttcaaat ctcaacgtgt    780
cactttgtgc aagataccca gaaaagagat ttgttcctga tggtaacaga atttcctggg    840
acagcaagaa gggctttact attcccagct acatgatcag ctatgctggc atggtcttct    900
gtgaagcaaa aattaatgat gaaagttacc agtctattat gtacatagtt gtcgttgtag    960
ggtataggat ttatgatgtg gttctgagtc cgtctcatgg aattgaacta tctgttggag   1020
aaaagcttgt cttaaattgt acagcaagaa ctgaactaaa tgtggggatt gacttcaact   1080
gggaataccc ttcttcgaag catcagcata agaaacttgt aaaccgagac ctaaaaaccc   1140
agtctgggag tgagatgaag aaatttttga gcaccttaac tatagatggt gtaacccgga   1200
gtgaccaagg attgtacacc tgtgcagcat ccagtgggct gatgaccaag aagaacagca   1260
catttgtcag ggtccatgaa aaaccttttg ttgcttttgg aagtggcatg gaatctctgg   1320
tggaagccac ggtgggggag cgtgtcagaa tccctgcgaa gtaccttggt tacccacccc   1380
cagaaataaa atggtataaa aatggaatac cccttgagtc caatcacaca attaaagcgg   1440
ggcatgtact gacgattatg gaagtgagtg aaagagacac aggaaattac actgtcatcc   1500
ttaccaatcc catttcaaag gagaagcaga gccatgtggt ctctctggtt gtgtatgtcc   1560
caccccagat tggtgagaaa tctctaatct ctcctgtgga ttcctaccag tacggcacca   1620
ctcaaacgct gacatgtacg gtctatgcca ttcctccccc gcatcacatc cactggtatt   1680
ggcagttgga ggaagagtgc gccaacgagc ccagccaagc tgtctcagtg acaaacccat   1740
acccttgtga agaatggaga agtgtggagg acttccaggg aggaaataaa attgaagtta   1800
ataaaaatca atttgctcta attgaaggaa aaaacaaaac tgtaagtacc cttgttatcc   1860
aagcggcaaa tgtgtcagct ttgtacaaat gtgaagcggt caacaaagtc gggagaggag   1920
agagggtgat ctccttccac gtgaccaggg gtcctgaaat tactttgcaa cctgacatgc   1980
agcccactga gcaggagagc gtgtctttgt ggtgcactgc agacagatct acgtttgaga   2040
acctcacatg gtacaagctt ggcccacagc ctctgccaat ccatgtggga gagttgccca   2100
cacctgtttg caagaacttg gatactcttt ggaaattgaa tgccaccatg ttctctaata   2160
gcacaaatga cattttgatc atggagctta agaatgcatc cttgcaggac caaggagact   2220
atgtctgcct tgctcaagac aggaagacca agaaaagaca ttgcgtggtc aggcagctca   2280
cagtcctaga gcgtgtggca cccacgatca caggaaacct ggagaatcag acgacaagta   2340
ttggggaaag catcgaagtc tcatgcacgg catctgggaa tccccctcca cagatcatgt   2400
ggtttaaaga taatgagacc cttgtagaag actcaggcat tgtattgaag gatgggaacc   2460
ggaacctcac tatccgcaga gtgaggaagg aggacgaagg cctctacacc tgccaggcat   2520
gcagtgttct tggctgtgca aaagtggagg catttttcat aatagaaggt gcccaggaaa   2580
```

```
agacgaactt ggaaatcatt attctagtag gcacggcggt gattgccatg ttcttctggc   2640
tacttcttgt catcatccta cggaccgtta agcgggccaa tggaggggaa ctgaagacag   2700
gctacttgtc catcgtcatg gatccagatg aactcccatt ggatgaacat tgtgaacgac   2760
tgccttatga tgccagcaaa tgggaattcc ccagagaccg gctgaagcta ggtaagcctc   2820
ttggccgtgg tgcctttggc caagtgattg aagcagatgc ctttggaatt gacaagacag   2880
caacttgcag gacagtagca gtcaaaatgt tgaaagaagg agcaacacac agtgagcatc   2940
gagctctcat gtctgaactc aagatcctca ttcatattgg tcaccatctc aatgtggtca   3000
accttctagg tgcctgtacc aagccaggag ggccactcat ggtgattgtg gaattctgca   3060
aatttggaaa cctgtccact tacctgagga gcaagagaaa tgaatttgtc ccctacaaga   3120
ccaaaggggc acgattccgt caagggaaag actacgttgg agcaatccct gtggatctga   3180
aacggcgctt ggacagcatc accagtagcc agagctcagc cagctctgga tttgtggagg   3240
agaagtccct cagtgatgta gaagaagagg aagctcctga agatctgtat aaggacttcc   3300
tgaccttgga gcatctcatc tgttacagct tccaagtggc taagggcatg gagttcttgg   3360
catcgcgaaa gtgtatccac agggacctgg cggcacgaaa tatcctctta tcggagaaga   3420
acgtggttaa aatctgtgac tttggcttgg cccgggatat ttataaagat ccagattatg   3480
tcagaaaagg agatgctcgc ctccctttga aatggatggc cccagaaaca atttttgaca   3540
gagtgtacac aatccagagt gacgtctggt cttttggtgt tttgctgtgg gaaatatttt   3600
ccttaggtgc ttctccatat cctggggtaa agattgatga agaattttgt aggcgattga   3660
aagaaggaac tagaatgagg gcccctgatt atactacacc agaaatgtac cagaccatgc   3720
tggactgctg gcacggggag cccagtcaga gacccacgtt ttcagagttg gtggaacatt   3780
tgggaaatct cttgcaagct aatgctcagc aggatggcaa agactacatt gttcttccga   3840
tatcagagac tttgagcatg gaagaggatt ctggactctc tctgcctacc tcacctgttt   3900
cctgtatgga ggaggaggaa gtatgtgacc ccaaattcca ttatgacaac acagcaggaa   3960
tcagtcagta tctgcagaac agtaagcgaa agagccggcc tgtgagtgta aaaacatttg   4020
aagatatccc gttagaagaa ccagaagtaa aagtaatccc agatgacaac cagacggaca   4080
gtggtatggt tcttgcctca gaagagctga aaactttgga agacagaacc aaattatctc   4140
catcttttgg tggaatggtg cccagcaaaa gcagggagtc tgtggcatct gaaggctcaa   4200
accagacaag cggctaccag tccggatatc actccgatga cacagacacc accgtgtact   4260
ccagtgagga agcagaactt ttaaagctga tagagattgg agtgcaaacc ggtagcacag   4320
cccagattct ccagcctgac tcggggacca cactgagctc tcctcctgtt taaaaggaag   4380
catccacacc cccaactcct ggacatcaca tgagaggtgc tgctcagatt ttcaagtgtt   4440
gttctttcca ccagcaggaa gtagccgcat ttgattttca tttcgacaac agaaaaagga   4500
cctcggactg cagggagcca gtcttctagg catatcctgg aagaggcttg tgacccaaga   4560
atgtgtctgt gtcttctccc agtgttgacc tgatcctctt tttcattcat ttaaaaagca   4620
tttatcatgc cccctgctgc gggtctcacc atgggtttag aacaaagacg ttcaagaaat   4680
ggccccatcc tcaaagaagt agcagtacct ggggagctga cacttctgta aaactagaag   4740
ataaaccagg caatgtaagt gttcgaggtg ttgaagatgg gaaggatttg cagggctgag   4800
tctatccaag aggctttgtt taggacgtgg gtcccaagcc aagccttaag tgtggaattc   4860
ggattgatag aaaggaagac taacgttacc ttgctttgga gagtactgga gcctgcaaat   4920
```

-continued

```
gcattgtgtt tgctctggtg gaggtgggca tggggtctgt tctgaaatgt aaagggttca   4980

gacggggttt ctggttttag aaggttgcgt gttcttcgag ttgggctaaa gtagagttcg   5040

ttgtgctgtt tctgactcct aatgagagtt ccttccagac cgttacgtgt ctcctggcca   5100

agccccagga aggaaatgat gcagctctgg ctccttgtct cccaggctga tcctttattc   5160

agaataccac aaagaaagga cattcagctc aaggctccct gccgtgttga agagttctga   5220

ctgcacaaac cagcttctgg tttcttctgg aatgaatacc ctcatatctg tcctgatgtg   5280

atatgtctga gactgaatgc gggaggttca atgtgaagct gtgtgtggtg tcaaagtttc   5340

aggaaggatt ttaccctttt gttcttcccc ctgtccccaa cccactctca ccccgcaacc   5400

catcagtatt ttagttattt ggcctctact ccagtaaacc tgattgggtt tgttcactct   5460

ctgaatgatt attagccaga cttcaaaatt attttatagc ccaaattata acatctattg   5520

tattatttag acttttaaca tatagagcta tttctactga tttttgccct tgttctgtcc   5580

ttttttttcaa aaaagaaaat gtgttttttg tttggtacca tagtgtgaaa tgctgggaac   5640

aatgactata agacatgcta tggcacatat atttatagtc tgtttatgta gaaacaaatg   5700

taatatatta aagccttata tataatgaac tttgtactat tcacattttg tatcagtatt   5760

atgtagcata acaaaggtca taatgctttc agcaattgat gtcattttat taaagaacat   5820

tgaaaaactt gaaggaatcc ctttgcaagg ttgcattact gtacccatca tttctaaaat   5880

ggaagagggg gtggctgggc acagtggccg acacctaaaa acccagcact ttggggggcc   5940

aaggtgggag gatcgcttga gcccaggagt tcaagaccag tctggccaac atggtcagat   6000

tccatctcaa agaaaaaagg taaaaataaa ataaaatgga gaagaaggaa tcaga        6055
```

<210> SEQ ID NO 3
<211> LENGTH: 5718
<212> TYPE: DNA
<213> ORGANISM: homo sapiens

<400> SEQUENCE: 3

```
ctcctgaggc tgccagcagc cagcagtgac tgcccgccct atctgggacc caggatcgct     60

ctgtgagcaa cttggagcca gagaggagat caacaaggag gaggagagag ccggcccctc    120

agccctgctg cccagcagca gcctgtgctc gccctgccca acgcagacag ccagacccag    180

ggcggcccct ctggcggctc tgctcctccc gaaggatgct tggggagtga ggcgaagctg    240

ggccgctcct ctcccctaca gcagcccccct tcctccatcc ctctgttctc ctgagccttc    300

aggagcctgc accagtcctg cctgtccttc tactcagctg ttacccactc tgggaccagc    360

agtctttctg ataactggga gagggcagta aggaggactt cctggagggg gtgactgtcc    420

agagcctgga actgtgccca caccagaagc catcagcagc aaggacacca tgcggcttcc    480

gggtgcgatg ccagctctgg ccctcaaagg cgagctgctg ttgctgtctc tcctgttact    540

tctggaacca cagatctctc agggcctggt cgtcacaccc ccggggccag agcttgtcct    600

caatgtctcc agcaccttcg ttctgacctg ctcgggttca gctccggtgg tgtgggaacg    660

gatgtcccag gagcccccac aggaaatggc caaggcccag gatggcacct tctccagcgt    720

gctcacactg accaacctca ctgggctaga cacgggagaa tacttttgca cccacaatga    780

ctcccgtgga ctggagaccg atgagcggaa acggctctac atctttgtgc cagatcccac    840

cgtgggcttc ctccctaatg atgccgagga actattcatc tttctcacgg aaataactga    900

gatcaccatt ccatgccgag taacagaccc acagctggtg gtgacactgc acgagaagaa    960

aggggacgtt gcactgcctg tcccctatga tcaccaacgt ggcttttctg gtatctttga   1020
```

```
ggacagaagc tacatctgca aaaccaccat tggggacagg gaggtggatt ctgatgccta   1080
ctatgtctac agactccagg tgtcatccat caacgtctct gtgaacgcag tgcagactgt   1140
ggtccgccag ggtgagaaca tcaccctcat gtgcattgtg atcgggaatg aggtggtcaa   1200
cttcgagtgg acatacccccc gcaaagaaag tgggcggctg gtggagccgg tgactgactt   1260
cctcttggat atgccttacc acatccgctc catcctgcac atccccagtg ccgagttaga   1320
agactcgggg acctacacct gcaatgtgac ggagagtgtg aatgaccatc aggatgaaaa   1380
ggccatcaac atcaccgtgg ttgagagcgg ctacgtgcgg ctcctgggag aggtgggcac   1440
actacaattt gctgagctgc atcggagccg gacactgcag gtagtgttcg aggcctaccc   1500
accgcccact gtcctgtggt tcaaagacaa ccgcaccctg ggcgactcca gcgctggcga   1560
aatcgccctg tccacgcgca acgtgtcgga gacccggtat gtgtcagagc tgacactggt   1620
tcgcgtgaag gtggcagagg ctggccacta caccatgcgg gccttccatg aggatgctga   1680
ggtccagctc tccttccagc tacagatcaa tgtccctgtc cgagtgctgg agctaagtga   1740
gagccaccct gacagtgggg aacagacagt ccgctgtcgt ggccggggca tgccccagcc   1800
gaacatcatc tggtctgcct gcagagacct caaaaggtgt ccacgtgagc tgccgcccac   1860
gctgctgggg aacagttccg aagaggagag ccagctggag actaacgtga cgtactggga   1920
ggaggagcag gagtttgagg tggtgagcac actgcgtctg cagcacgtgg atcggccact   1980
gtcggtgcgc tgcacgctgc gcaacgctgt gggccaggac acgcaggagg tcatcgtggt   2040
gccacactcc ttgcccttta aggtggtggt gatctcagcc atcctggccc tggtggtgct   2100
caccatcatc tcccttatca tcctcatcat gctttggcag aagaagccac gttacgagat   2160
ccgatggaag gtgattgagt ctgtgagctc tgacggccat gagtacatct acgtggaccc   2220
catgcagctg ccctatgact ccacgtggga gctgccgcgg gaccagcttg tgctgggacg   2280
caccctcggc tctggggcct ttgggcaggt ggtggaggcc acggctcatg gcctgagcca   2340
ttctcaggcc acgatgaaag tggccgtcaa gatgcttaaa tccacagccc gcagcagtga   2400
gaagcaagcc cttatgtcgg agctgaagat catgagtcac cttgggcccc acctgaacgt   2460
ggtcaacctg ttgggggcct gcaccaaagg aggacccatc tatatcatca ctgagtactg   2520
ccgctacgga gacctggtgg actacctgca ccgcaacaaa cacaccttcc tgcagcacca   2580
ctccgacaag cgccgcccgc ccagcgcgga gctctacagc aatgctctgc ccgttgggct   2640
ccccctgccc agccatgtgt ccttgaccgg ggagagcgac ggtggctaca tggacatgag   2700
caaggacgag tcggtggact atgtgcccat gctggacatg aaaggagacg tcaaatatgc   2760
agacatcgag tcctccaact acatggcccc ttacgataac tacgttccct ctgcccctga   2820
gaggacctgc cgagcaactt tgatcaacga gtctccagtg ctaagctaca tggacctcgt   2880
gggcttcagc taccaggtgg ccaatggcat ggagtttctg gcctccaaga actgcgtcca   2940
cagagacctg gcggctagga acgtgctcat ctgtgaaggc aagctggtca agatctgtga   3000
ctttggcctg gctcgagaca tcatgcggga ctcgaattac atctccaaag gcagcacctt   3060
tttgccttta aagtggatgg ctccggagag catcttcaac agcctctaca ccaccctgag   3120
cgacgtgtgg tccttcggga tcctgctctg ggagatcttc accttgggtg gcacccctta   3180
cccagagctg cccatgaacg agcagttcta caatgccatc aaacggggtt accgcatggc   3240
ccagcctgcc catgcctccg acgagatcta tgagatcatg cagaagtgct gggaagagaa   3300
gtttgagatt cggcccccct tctcccagct ggtgctgctt ctcgagagac tgttgggcga   3360
```

-continued

```
aggttacaaa aagaagtacc agcaggtgga tgaggagttt ctgaggagtg accacccagc   3420
catccttcgg tcccaggccc gcttgcctgg gttccatggc ctccgatctc ccctggacac   3480
cagctccgtc ctctatactg ccgtgcagcc caatgagggt gacaacgact atatcatccc   3540
cctgcctgac cccaaacccg aggttgctga cgagggccca ctggagggtt cccccagcct   3600
agccagctcc accctgaatg aagtcaacac ctcctcaacc atctcctgtg acagcccccct  3660
ggagccccag gacgaaccag agccagagcc ccagcttgag ctccaggtgg agccggagcc   3720
agagctggaa cagttgccgg attcggggtg ccctgcgcct cgggcggaag cagaggatag   3780
cttcctgtag gggggctggcc cctaccctgc cctgcctgaa gctcccccccc tgccagcacc 3840
cagcatctcc tggcctggcc tgaccgggct tcctgtcagc caggctgccc ttatcagctg   3900
tccccttctg gaagctttct gctcctgacg tgttgtgccc caaaccctgg ggctggctta   3960
ggaggcaaga aaactgcagg ggccgtgacc agccctctgc ctccagggag gccaactgac   4020
tctgagccag ggttcccccca gggaactcag ttttcccata tgtaagatgg gaaagttagg  4080
cttgatgacc cagaatctag gattctctcc ctggctgaca ggtggggaga ccgaatccct   4140
ccctgggaag attcttggag ttactgaggt ggtaaattaa ctttttttctg ttcagccagc  4200
taccccctcaa ggaatcatag ctctctcctc gcactttttat ccacccagga gctagggaag 4260
agaccctagc ctccctggct gctggctgag ctagggccta gccttgagca gtgttgcctc   4320
atccagaaga aagccagtct cctccctatg atgccagtcc ctgcgttccc tggcccgagc   4380
tggtctgggg ccattaggca gcctaattaa tgctggaggc tgagccaagt acaggacacc   4440
cccagcctgc agcccttgcc cagggcactt ggagcacacg cagccatagc aagtgcctgt   4500
gtccctgtcc ttcaggccca tcagtcctgg ggctttttct ttatcaccct cagtcttaat   4560
ccatccacca gagtctagaa ggccagacgg gccccgcatc tgtgatgaga atgtaaatgt   4620
gccagtgtgg agtggccacg tgtgtgtgcc agtatatggc cctggctctg cattggacct   4680
gctatgaggc tttggaggaa tccctcaccc tctctgggcc tcagtttccc cttcaaaaaa   4740
tgaataagtc ggacttatta actctgagtg ccttgccagc actaacattc tagagtattc   4800
caggtggttg cacatttgtc cagatgaagc aaggccatat accctaaact tccatcctgg   4860
gggtcagctg ggctcctggg agattccaga tcacacatca cactctgggg actcaggaac   4920
catgcccctt ccccaggccc ccagcaagtc tcaagaacac agctgcacag gccttgactt   4980
agagtgacag ccggtgtcct ggaaagcccc cagcagctgc cccagggaca tgggaagacc   5040
acgggacctc tttcactacc cacgatgacc tccgggggta tcctgggcaa aagggacaaa   5100
gagggcaaat gagatcacct cctgcagccc accactccag cacctgtgcc gaggtctgcg   5160
tcgaagacag aatggacagt gaggacagtt atgtcttgta aaagacaaga agcttcagat   5220
gggtacccca agaaggatgt gagaggtggg cgctttggag gtttgcccct cacccaccag   5280
ctgccccatc cctgaggcag cgctccatgg gggtatggtt ttgtcactgc ccagacctag   5340
cagtgacatc tcattgtccc cagcccagtg ggcattggag gtgccagggg agtcagggtt   5400
gtagccaaga cgcccccgca cggggagggt tgggaagggg gtgcaggaag ctcaacccct   5460
ctgggcacca accctgcatt gcaggttggc accttacttc cctgggatcc ccagagttgg   5520
tccaaggagg gagagtgggt tctcaatacg gtaccaaaga tataatcacc taggtttaca   5580
aatattttta ggactcacgt taactcacat ttatacagca gaaatgctat tttgtatgct   5640
gttaagtttt tctatctgtg tactttttttt taagggaaag attttaatat taaacctggt  5700
gcttctcact cacaaaaa                                                  5718
```

<210> SEQ ID NO 4
<211> LENGTH: 5190
<212> TYPE: DNA
<213> ORGANISM: homo sapiens

<400> SEQUENCE: 4

```
tctgggggct cggctttgcc gcgctcgctg cacttgggcg agagctggaa cgtggaccag     60
agctcggatc ccatcgcagc taccgcgatg agaggcgctc gcggcgcctg ggattttctc    120
tgcgttctgc tcctactgct tcgcgtccag acaggctctt ctcaaccatc tgtgagtcca    180
ggggaaccgt ctccaccatc catccatcca ggaaaatcag acttaatagt ccgcgtgggc    240
gacgagatta ggctgttatg cactgatccg ggctttgtca aatggacttt tgagatcctg    300
gatgaaacga atgagaataa gcagaatgaa tggatcacgg aaaaggcaga agccaccaac    360
accggcaaat acacgtgcac caacaaacac ggcttaagca attccattta tgtgtttgtt    420
agagatcctg ccaagctttt ccttgttgac cgctccttgt atgggaaaga agacaacgac    480
acgctggtcc gctgtcctct cacagaccca gaagtgacca attattccct caaggggtgc    540
caggggaagc ctcttcccaa ggacttgagg tttattcctg accccaaggc gggcatcatg    600
atcaaaagtg tgaaacgcgc ctaccatcgg ctctgtctgc attgttctgt ggaccaggag    660
ggcaagtcag tgctgtcgga aaaattcatc ctgaaagtga ggccagcctt caaagctgtg    720
cctgttgtgt ctgtgtccaa agcaagctat cttcttaggg aaggggaaga attcacagtg    780
acgtgcacaa taaaagatgt gtctagttct gtgtactcaa cgtggaaaag agaaaacagt    840
cagactaaac tacaggagaa atataatagc tggcatcacg gtgacttcaa ttatgaacgt    900
caggcaacgt tgactatcag ttcagcgaga gttaatgatt ctggagtgtt catgtgttat    960
gccaataata cttttggatc agcaaatgtc acaacaacct tggaagtagt agataaagga   1020
ttcattaata tcttccccat gataaacact acagtatttg taaacgatgg agaaaatgta   1080
gatttgattg ttgaatatga agcattcccc aaacctgaac accagcagtg gatctatatg   1140
aacagaacct tcactgataa atgggaagat tatcccaagt ctgagaatga aagtaatatc   1200
agatacgtaa gtgaacttca tctaacgaga ttaaaaggca ccgaaggagg cacttacaca   1260
ttcctagtgt ccaattctga cgtcaatgct gccatagcat ttaatgttta tgtgaataca   1320
aaaccagaaa tcctgactta cgacaggctc gtgaatggca tgctccaatg tgtggcagca   1380
ggattcccag agcccacaat agattggtat ttttgtccag gaactgagca gagatgctct   1440
gcttctgtac tgccagtgga tgtgcagaca ctaaactcat ctgggccacc gtttggaaag   1500
ctagtggttc agagttctat agattctagt gcattcaagc acaatggcac ggttgaatgt   1560
aaggcttaca acgatgtggg caagacttct gcctatttta actttgcatt taaaggtaac   1620
aacaaagagc aaatccatcc ccacaccctg ttcactcctt tgctgattgg tttcgtaatc   1680
gtagctggca tgatgtgcat tattgtgatg attctgacct acaaatattt acagaaaccc   1740
atgtatgaag tacagtggaa ggttgttgag gagataaatg gaaacaatta tgtttacata   1800
gacccaacac aacttcctta tgatcacaaa tgggagtttc ccagaaacag gctgagtttt   1860
gggaaaaccc tgggtgctgg agctttcggg aaggttgttg aggcaactgc ttatggctta   1920
attaagtcag atgcggccat gactgtcgct gtaaagatgc tcaagccgag tgcccatttg   1980
acagaacggg aagccctcat gtctgaactc aaagtcctga gttaccttgg taatcacatg   2040
aatattgtga atctacttgg agcctgcacc attggagggc ccaccctggt cattacagaa   2100
```

```
tattgttgct atggtgatct tttgaatttt ttgagaagaa aacgtgattc atttatttgt   2160
tcaaagcagg aagatcatgc agaagctgca ctttataaga atcttctgca ttcaaaggag   2220
tcttcctgca gcgatagtac taatgagtac atggacatga aacctggagt ttcttatgtt   2280
gtcccaacca aggccgacaa aaggagatct gtgagaatag gctcatacat agaaagagat   2340
gtgactcccg ccatcatgga ggatgacgag ttggccctag acttagaaga cttgctgagc   2400
ttttcttacc aggtggcaaa gggcatggct ttcctcgcct ccaagaattg tattcacaga   2460
gacttggcag ccagaaatat cctccttact catggtcgga tcacaaagat ttgtgatttt   2520
ggtctagcca gagacatcaa gaatgattct aattatgtgg ttaaaggaaa cgctcgacta   2580
cctgtgaagt ggatggcacc tgaaagcatt ttcaactgtg tatacacgtt tgaaagtgac   2640
gtctggtcct atgggatttt tctttgggag ctgttctctt taggaagcag cccctatcct   2700
ggaatgccgg tcgattctaa gttctacaag atgatcaagg aaggcttccg gatgctcagc   2760
cctgaacacg cacctgctga aatgtatgac ataatgaaga cttgctggga tgcagatccc   2820
ctaaaaagac caacattcaa gcaaattgtt cagctaattg agaagcagat ttcagagagc   2880
accaatcata tttactccaa cttagcaaac tgcagcccca accgacagaa gcccgtggta   2940
gaccattctg tgcggatcaa ttctgtcggc agcaccgctt cctcctccca gcctctgctt   3000
gtgcacgacg atgtctgagc agaatcagtg tttgggtcac ccctccagga atgatctctt   3060
cttttggctt ccatgatggt tattttcttt tctttcaact tgcatccaac tccaggatag   3120
tgggcacccc actgcaatcc tgtctttctg agcacacttt agtggccgat gatttttgtc   3180
atcagccacc atcctattgc aaaggttcca actgtatata ttcccaatag caacgtagct   3240
tctaccatga acagaaaaca ttctgatttg gaaaaagaga gggaggtatg gactgggggc   3300
cagagtcctt tccaaggctt ctccaattct gcccaaaaat atggttgata gtttacctga   3360
ataaatggta gtaatcacag ttggccttca gaaccatcca tagtagtatg atgatacaag   3420
attagaagct gaaaacctaa gtcctttatg tggaaaacag aacatcatta gaacaaagga   3480
cagagtatga acacctgggc ttaagaaatc tagtatttca tgctgggaat gagacatagg   3540
ccatgaaaaa aatgatcccc aagtgtgaac aaaagatgct cttctgtgga ccactgcatg   3600
agcttttata ctaccgacct ggtttttaaa tagagtttgc tattagagca ttgaattgga   3660
gagaaggcct ccctagccag cacttgtata tacgcatcta taaattgtcc gtgttcatac   3720
atttgagggg aaaacaccat aaggtttcgt ttctgtatac aaccctggca ttatgtccac   3780
tgtgtataga agtagattaa gagccatata agtttgaagg aaacagttaa taccattttt   3840
taaggaaaca atataaccac aaagcacagt ttgaacaaaa tctcctcttt tagctgatga   3900
acttattctg tagattctgt ggaacaagcc tatcagcttc agaatggcat tgtactcaat   3960
ggatttgatg ctgtttgaca aagttactga ttcactgcat ggctcccaca ggagtgggaa   4020
aacactgcca tcttagtttg gattcttatg tagcaggaaa taaagtatag gtttagcctc   4080
cttcgcaggc atgtcctgga caccgggcca gtatctatat atgtgtatgt acgtttgtat   4140
gtgtgtagac aaatatttgg aggggtattt ttgccctgag tccaagaggg tcctttagta   4200
cctgaaaagt aacttggctt tcattattag tactgctctt gtttcttttc acatagctgt   4260
ctagagtagc ttaccagaag cttccatagt ggtgcagagg aagtggaagg catcagtccc   4320
tatgtatttg cagttcacct gcacttaagg cactctgtta tttagactca tcttactgta   4380
cctgttcctt agaccttcca taatgctact gtctcactga aacatttaaa ttttaccctt   4440
tagactgtag cctggatatt attcttgtag tttacctctt taaaaacaaa acaaaacaaa   4500
```

```
acaaaaaact ccccttcctc actgcccaat ataaaaggca aatgtgtaca tggcagagtt   4560

tgtgtgttgt cttgaaagat tcaggtatgt tgcctttatg gtttcccccct tctacatttc   4620

ttagactaca tttagagaac tgtggccgtt atctggaagt aaccatttgc actggagttc   4680

tatgctctcg cacctttcca aagttaacag attttggggt tgtgttgtca cccaagagat   4740

tgttgtttgc catactttgt ctgaaaaatt cctttgtgtt tctattgact tcaatgatag   4800

taagaaaagt ggttgttagt tatagatgtc taggtacttc aggggcactt cattgagagt   4860

tttgtcttgg atattcttga aagtttatat ttttataatt ttttcttaca tcagatgttt   4920

ctttgcagtg gcttaatgtt tgaaattatt ttgtggcttt ttttgtaaat attgaaatgt   4980

agcaataatg tcttttgaat attcccaagc ccatgagtcc ttgaaaatat tttttatata   5040

tacagtaact ttatgtgtaa atacataagc ggcgtaagtt taaaggatgt tggtgttcca   5100

cgtgttttat tcctgtatgt tgtccaattg ttgacagttc tgaagaattc taataaaatg   5160

tacatatata aatcaaaaaa aaaaaaaaaa                                    5190
```

<210> SEQ ID NO 5
<211> LENGTH: 3291
<212> TYPE: DNA
<213> ORGANISM: homo sapiens

<400> SEQUENCE: 5

```
agaatcggag agccggtggc gtcgcaggtc gggaggacga gcaccgagtc gagggctcgc     60

tcgtctgggc cgcccgagag tcttaatcgc gggcgcttgg gccgccatct tagatggcgg    120

gagtaagagg aaaacgattg tgaggcggga acggctttct gctgcctttt ttgggccccg    180

aaaagggtca gctggccggg ctttggggcg cgtgccctga ggcgcggagc gcgtttgcta    240

cgatgcgggg gctgctcggg gctccgtccc ctgggctggg gacgcgccga atgtgaccgc    300

ctcccgctcc ctcacccgcc gcggggagga ggagcgggcg agaagctgcc gccgaacgac    360

aggacgttgg ggcggcctgg ctccctcagg tttaagaatt gtttaagctg catcaatgga    420

gcacatacag ggagcttgga agacgatcag caatggtttt ggattcaaag atgccgtgtt    480

tgatggctcc agctgcatct ctcctacaat agttcagcag tttggctatc agcgccgggc    540

atcagatgat ggcaaactca cagatccttc taagacaagc aacactatcc gtgttttctt    600

gccgaacaag caaagaacag tggtcaatgt gcgaaatgga atgagcttgc atgactgcct    660

tatgaaagca ctcaaggtga ggggcctgca accagagtgc tgtgcagtgt tcagacttct    720

ccacgaacac aaaggtaaaa aagcacgctt agattggaat actgatgctg cgtctttgat    780

tggagaagaa cttcaagtag atttcctgga tcatgttccc ctcacaacac acaactttgc    840

tcggaagacg ttcctgaagc ttgccttctg tgacatctgt cagaaattcc tgctcaatgg    900

atttcgatgt cagacttgtg gctacaaatt tcatgagcac tgtagcacca aagtacctac    960

tatgtgtgtg gactggagta acatcagaca actcttattg tttccaaatt ccactattgg   1020

tgatagtgga gtcccagcac taccttcttt gactatgcgt cgtatgcgag agtctgtttc   1080

caggatgcct gttagttctc agcacagata ttctacacct cacgccttca cctttaacac   1140

ctccagtccc tcatctgaag gttccctctc ccagaggcag aggtcgacat ccacacctaa   1200

tgtccacatg gtcagcacca ccctgcctgt ggacagcagg atgattgagg atgcaattcg   1260

aagtcacagc gaatcagcct caccttcagc cctgtccagt agccccaaca atctgagccc   1320

aacaggctgg tcacagccga aaccccccgt gccagcacaa agagagcggg caccagtatc   1380
```

```
tgggacccag gagaaaaaca aaattaggcc tcgtggacag agagattcaa gctattattg   1440

ggaaatagaa gccagtgaag tgatgctgtc cactcggatt gggtcaggct cttttggaac   1500

tgtttataag ggtaaatggc acggagatgt tgcagtaaag atcctaaagg ttgtcgaccc   1560

aaccccagag caattccagg ccttcaggaa tgaggtggct gttctgcgca aaacacggca   1620

tgtgaacatt ctgcttttca tggggtacat gacaaaggac aacctggcaa ttgtgaccca   1680

gtggtgcgag ggcagcagcc tctacaaaca cctgcatgtc caggagacca agtttcagat   1740

gttccagcta attgacattg cccggcagac ggctcaggga atggactatt tgcatgcaaa   1800

gaacatcatc catagagaca tgaaatccaa caatatattt ctccatgaag gcttaacagt   1860

gaaaattgga gattttggtt tggcaacagt aaagtcacgc tggagtggtt ctcagcaggt   1920

tgaacaacct actggctctg tcctctggat ggccccagag gtgatccgaa tgcaggataa   1980

caacccattc agtttccagt cggatgtcta ctcctatggc atcgtattgt atgaactgat   2040

gacgggggag cttccttatt ctcacatcaa caaccgagat cagatcatct tcatggtggg   2100

ccgaggatat gcctccccag atcttagtaa gctatataag aactgcccca aagcaatgaa   2160

gaggctggta gctgactgtg tgaagaaagt aaaggaagag aggcctcttt ttccccagat   2220

cctgtcttcc attgagctgc tccaacactc tctaccgaag atcaaccgga gcgcttccga   2280

gccatccttg catcgggcag cccacactga ggatatcaat gcttgcacgc tgaccacgtc   2340

cccgaggctg cctgtcttct agttgacttt gcacctgtct tcaggctgcc aggggaggag   2400

gagaagccag caggcaccac ttttctgctc cctttctcca gaggcagaac acatgttttc   2460

agagaagctg ctgctaagga ccttctagac tgctcacagg gccttaactt catgttgcct   2520

tcttttctat ccctttgggc cctgggagaa ggaagccatt tgcagtgctg gtgtgtcctg   2580

ctccctcccc acattcccca tgctcaaggc ccagccttct gtagatgcgc aagtggatgt   2640

tgatggtagt acaaaaagca ggggcccagc cccagctgtt ggctacatga gtatttagag   2700

gaagtaaggt agcaggcagt ccagccctga tgtggagaca catgggattt tggaaatcag   2760

cttctggagg aatgcatgtc acaggcggga ctttcttcag agagtggtgc agcgccagac   2820

attttgcaca taaggcacca aacagcccag gactgccgag actctggccg cccgaaggag   2880

cctgctttgg tactatggaa cttttcttag ggacacgtcc tcctttcac agcttctaag   2940

gtgtccagtg cattgggatg gttttccagg caaggcactc ggccaatccg catctcagcc   3000

ctctcaggga gcagtcttcc atcatgctga attttgtctt ccaggagctg cccctatggg   3060

gcggggccgc agggccagcc ttgtttctct aacaaacaaa caaacaaaca gccttgtttc   3120

tctagtcaca tcatgtgtat acaaggaagc caggaataca ggttttcttg atgatttggg   3180

ttttaatttt gtttttattg cacctgacaa aatacagtta tctgatggtc cctcaattat   3240

gttattttaa taaaataaat taaatttagg tgtaaaaaaa aaaaaaaaaa a            3291
```

<210> SEQ ID NO 6
<211> LENGTH: 5616
<212> TYPE: DNA
<213> ORGANISM: homo sapiens

<400> SEQUENCE: 6

```
ccccggcgca gcgcggccgc agcagcctcc gcccccgca cggtgtgagc gcccgacgcg      60

gccgaggcgg ccggagtccc gagctagccc cggcggccgc cgccgcccag accggacgac    120

aggccacctc gtcggcgtcc gcccgagtcc ccgcctcgcc gccaacgcca caaccaccgc    180

gcacggcccc ctgactccgt ccagtattga tcgggagagc cggagcgagc tcttcgggga    240
```

```
gcagcgatgc gaccctccgg gacggccggg gcagcgctcc tggcgctgct ggctgcgctc    300
tgcccggcga gtcgggctct ggaggaaaag aaagtttgcc aaggcacgag taacaagctc    360
acgcagttgg gcacttttga agatcatttt ctcagcctcc agaggatgtt caataactgt    420
gaggtggtcc ttgggaattt ggaaattacc tatgtgcaga ggaattatga tctttccttc    480
ttaaagacca tccaggaggt ggctggttat gtcctcattg ccctcaacac agtggagcga    540
attcctttgg aaaacctgca gatcatcaga ggaaatatgt actacgaaaa ttcctatgcc    600
ttagcagtct tatctaacta tgatgcaaat aaaaccggac tgaaggagct gcccatgaga    660
aatttacagg aaatcctgca tggcgccgtg cggttcagca acaaccctgc cctgtgcaac    720
gtggagagca tccagtggcg ggacatagtc agcagtgact ttctcagcaa catgtcgatg    780
gacttccaga accacctggg cagctgccaa aagtgtgatc caagctgtcc caatgggagc    840
tgctggggtg caggagagga gaactgccag aaactgacca aaatcatctg tgcccagcag    900
tgctccgggc gctgccgtgg caagtccccc agtgactgct gccacaacca gtgtgctgca    960
ggctgcacag gcccccggga gagcgactgc ctggtctgcc gcaaattccg agacgaagcc   1020
acgtgcaagg acacctgccc cccactcatg ctctacaacc ccaccacgta ccagatggat   1080
gtgaaccccg agggcaaata cagctttggt gccacctgcg tgaagaagtg tccccgtaat   1140
tatgtggtga cagatcacgg ctcgtgcgtc cgagcctgtg gggccgacag ctatgagatg   1200
gaggaagacg gcgtccgcaa gtgtaagaag tgcgaagggc cttgccgcaa agtgtgtaac   1260
ggaataggta ttggtgaatt taaagactca ctctccataa atgctacgaa tattaaacac   1320
ttcaaaaact gcacctccat cagtggcgat ctccacatcc tgccggtggc atttaggggt   1380
gactccttca cacatactcc tcctctggat ccacaggaac tggatattct gaaaaccgta   1440
aaggaaatca cagggttttt gctgattcag gcttggcctg aaaacaggac ggacctccat   1500
gcctttgaga acctagaaat catacgcggc aggaccaagc aacatggtca gttttctctt   1560
gcagtcgtca gcctgaacat aacatccttg ggattacgct ccctcaagga gataagtgat   1620
ggagatgtga taatttcagg aaacaaaaat ttgtgctatg caaatacaat aaactggaaa   1680
aaactgtttg ggacctccgg tcagaaaacc aaaattataa gcaacagagg tgaaaacagc   1740
tgcaaggcca caggccaggt ctgccatgcc ttgtgctccc ccgagggctg ctggggcccg   1800
gagcccaggg actgcgtctc ttgccggaat gtcagccgag gcagggaatg cgtggacaag   1860
tgcaaccttc tggagggtga gccaagggag tttgtggaga actctgagtg catacagtgc   1920
cacccagagt gcctgcctca ggccatgaac atcacctgca caggacgggg accagacaac   1980
tgtatccagt gtgcccacta cattgacggc ccccactgcg tcaagacctg cccggcagga   2040
gtcatgggag aaaacaacac cctggtctgg aagtacgcag acgccggcca tgtgtgccac   2100
ctgtgccatc caaactgcac ctacggatgc actgggccag gtcttgaagg ctgtccaacg   2160
aatgggccta agatcccgtc catcgccact gggatggtgg gggccctcct cttgctgctg   2220
gtggtggccc tggggatcgg cctcttcatg cgaaggcgcc acatcgttcg gaagcgcacg   2280
ctgcggaggc tgctgcagga gagggagctt gtggagcctc ttacacccag tggagaagct   2340
cccaaccaag ctctcttgag gatcttgaag gaaactgaat tcaaaaagat caaagtgctg   2400
ggctccggtg cgttcggcac ggtgtataag ggactctgga tcccagaagg tgagaaagtt   2460
aaaattcccg tcgctatcaa ggaattaaga gaagcaacat ctccgaaagc caacaaggaa   2520
atcctcgatg aagcctacgt gatggccagc gtggacaacc cccacgtgtg ccgcctgctg   2580
```

-continued

```
ggcatctgcc tcacctccac cgtgcagctc atcacgcagc tcatgccctt cggctgcctc   2640
ctggactatg tccgggaaca caaagacaat attggctccc agtacctgct caactggtgt   2700
gtgcagatcg caaagggcat gaactacttg gaggaccgtc gcttggtgca ccgcgacctg   2760
gcagccagga acgtactggt gaaaacaccg cagcatgtca agatcacaga ttttgggctg   2820
gccaaactgc tgggtgcgga agagaaagaa taccatgcag aaggaggcaa agtgcctatc   2880
aagtggatgg cattggaatc aattttacac agaatctata cccaccagag tgatgtctgg   2940
agctacgggg tgaccgtttg ggagttgatg acctttggat ccaagccata tgacggaatc   3000
cctgccagcg agatctcctc catcctggag aaaggagaac gcctccctca gccacccata   3060
tgtaccatcg atgtctacat gatcatggtc aagtgctgga tgatagacgc agatagtcgc   3120
ccaaagttcc gtgagttgat catcgaattc tccaaaatgg cccgagaccc ccagcgctac   3180
cttgtcattc agggggatga aagaatgcat ttgccaagtc ctacagactc caacttctac   3240
cgtgccctga tggatgaaga agacatggac gacgtggtgg atgccgacga gtacctcatc   3300
ccacagcagg gcttcttcag cagcccctcc acgtcacgga ctcccctcct gagctctctg   3360
agtgcaacca gcaacaattc caccgtggct tgcattgata gaaatgggct gcaaagctgt   3420
cccatcaagg aagacagctt cttgcagcga tacagctcag accccacagg cgccttgact   3480
gaggacagca tagacgacac cttcctccca gtgcctgaat acataaacca gtccgttccc   3540
aaaaggcccg ctggctctgt gcagaatcct gtctatcaca atcagcctct gaaccccgcg   3600
cccagcagag acccacacta ccaggacccc cacagcactg cagtgggcaa ccccgagtat   3660
ctcaacactg tccagcccac ctgtgtcaac agcacattcg acagccctgc ccactgggcc   3720
cagaaaggca gccaccaaat tagcctggac aaccctgact accagcagga cttctttccc   3780
aaggaagcca agccaaatgg catctttaag ggctccacag ctgaaaatgc agaataccta   3840
agggtcgcgc cacaaagcag tgaatttatt ggagcatgac cacggaggat agtatgagcc   3900
ctaaaaatcc agactctttc gatacccagg accaagccac agcaggtcct ccatcccaac   3960
agccatgccc gcattagctc ttagacccac agactggttt tgcaacgttt acaccgacta   4020
gccaggaagt acttccacct cgggcacatt ttgggaagtt gcattccttt gtcttcaaac   4080
tgtgaagcat ttacagaaac gcatccagca agaatattgt ccctttgagc agaaatttat   4140
ctttcaaaga ggtatatttg aaaaaaaaaa aaagtatatg tgaggatttt tattgattgg   4200
ggatcttgga gtttttcatt gtcgctattg atttttactt caatgggctc ttccaacaag   4260
gaagaagctt gctggtagca cttgctaccc tgagttcatc caggcccaac tgtgagcaag   4320
gagcacaagc cacaagtctt ccagaggatg cttgattcca gtggttctgc ttcaaggctt   4380
ccactgcaaa acactaaaga tccaagaagg ccttcatggc cccagcaggc cggatcggta   4440
ctgtatcaag tcatggcagg tacagtagga taagccactc tgtcccttcc tgggcaaaga   4500
agaaacggag gggatggaat tcttccttag acttactttt gtaaaaatgt ccccacggta   4560
cttactcccc actgatggac cagtggtttc cagtcatgag cgttagactg acttgtttgt   4620
cttccattcc attgttttga aactcagtat gctgcccctg tcttgctgtc atgaaatcag   4680
caagagagga tgacacatca aataataact cggattccag cccacattgg attcatcagc   4740
atttggacca atagcccaca gctgagaatg tggaatacct aaggatagca ccgcttttgt   4800
tctcgcaaaa acgtatctcc taatttgagg ctcagatgaa atgcatcagg tcctttgggg   4860
catagatcag aagactacaa aaatgaagct gctctgaaat ctcctttagc catcacccca   4920
accccccaaa attagtttgt gttacttatg gaagatagtt ttctcctttt acttcacttc   4980
```

```
aaaagctttt tactcaaaga gtatatgttc cctccaggtc agctgccccc aaaccccctc   5040
cttacgcttt gtcacacaaa aagtgtctct gccttgagtc atctattcaa gcacttacag   5100
ctctggccac aacagggcat tttacaggtg cgaatgacag tagcattatg agtagtgtgg   5160
aattcaggta gtaaatatga aactagggtt tgaaattgat aatgctttca caacatttgc   5220
agatgtttta gaaggaaaaa agttccttcc taaaataatt tctctacaat tggaagattg   5280
gaagattcag ctagttagga gcccaccttt tttcctaatc tgtgtgtgcc ctgtaacctg   5340
actggttaac agcagtcctt tgtaaacagt gttttaaact ctcctagtca atatccaccc   5400
catccaattt atcaaggaag aaatggttca gaaaatattt tcagcctaca gttatgttca   5460
gtcacacaca catacaaaat gttccttttg cttttaaagt aatttttgac tcccagatca   5520
gtcagagccc ctacagcatt gttaagaaag tatttgattt ttgtctcaat gaaaataaaa   5580
ctatattcat ttccactcta aaaaaaaaaa aaaaaa                              5616
```

```
<210> SEQ ID NO 7
<211> LENGTH: 8733
<212> TYPE: DNA
<213> ORGANISM: homo sapiens

<400> SEQUENCE: 7

gctcccggct tagaggacag cggggaaggc gggcggtggg gcaggggggcc tgaagcggcg     60
gtaccggtgc tggcggcggc agctgaggcc ttggccgaag ccgcgcgaac ctcagggcaa    120
gatgcttgga accggacctg ccgccgccac caccgctgcc accacatcta gcaatgtgag    180
cgtcctgcag cagtttgcca gtggcctaaa gagccggaat gaggaaacca gggccaaagc    240
cgccaaggag ctccagcact atgtcaccat ggaactccga gagatgagtc aagaggagtc    300
tactcgcttc tatgaccaac tgaaccatca catttttgaa ttggtttcca gctcagatgc    360
caatgagagg aaaggtggca tcttggccat agctagcctc ataggagtgg aaggtgggaa    420
tgccacccga attggcagat ttgccaacta tcttcggaac ctcctcccct ccaatgaccc    480
agttgtcatg gaaatggcat ccaaggccat tggccgtctt gccatggcag gggacacttt    540
taccgctgag tacgtggaat ttgaggtgaa gcgagccctg gaatggctgg gtgctgaccg    600
caatgagggc cggagacatg cagctgtcct ggttctccgt gagctggcca tcagcgtccc    660
taccttcttc ttccagcaag tgcaaccctt ctttgacaac atttttgtgg ccgtgtggga    720
ccccaaacag gccatccgtg agggagctgt agccgccctt cgtgcctgtc tgattctcac    780
aacccagcgt gagccgaagg agatgcagaa gcctcagtgg tacaggcaca catttgaaga    840
agcagagaag ggatttgatg agaccttggc caaagagaag ggcatgaatc gggatgatcg    900
gatccatgga gccttgttga tccttaacga gctggtccga atcagcagca tggagggaga    960
gcgtctgaga gaagaaatgg aagaaatcac acagcagcag ctggtacacg acaagtactg   1020
caaagatctc atgggcttcg gaacaaaacc tcgtcacatt accccccttca ccagtttcca   1080
ggctgtacag ccccagcagt caaatgcctt ggtggggctg ctggggtaca gctctcacca   1140
aggcctcatg ggatttggga cctcccccag tccagctaag tccaccctgg tggagagccg   1200
gtgttgcaga gacttgatgg aggagaaatt tgatcaggtg tgccagtggg tgctgaaatg   1260
caggaatagc aagaactcgc tgatccaaat gacaatcctt aatttgttgc cccgcttggc   1320
tgcattccga ccttctgcct tcacagatac ccagtatctc caagatacca tgaaccatgt   1380
cctaagctgt gtcaagaagg agaaggaacg tacagcggcc ttccaagccc tggggctact   1440
```

```
ttctgtggct gtgaggtctg agtttaaggt ctatttgcct cgcgtgctgg acatcatccg   1500
agcggccctg cccccaaagg acttcgccca taagaggcag aaggcaatgc aggtggatgc   1560
cacagtcttc acttgcatca gcatgctggc tcgagcaatg gggccaggca tccagcagga   1620
tatcaaggag ctgctggagc ccatgctggc agtgggacta agccctgccc tcactgcagt   1680
gctctacgac ctgagccgtc agattccaca gctaaagaag gacattcaag atgggctact   1740
gaaaatgctg tccctggtcc ttatgcacaa accccttcgc cacccaggca tgcccaaggg   1800
cctggcccat cagctggcct ctcctggcct cacgaccctc cctgaggcca gcgatgtggg   1860
cagcatcact cttgccctcc gaacgcttgg cagctttgaa tttgaaggcc actctctgac   1920
ccaatttgtt cgccactgtg cggatcattt cctgaacagt gagcacaagg agatccgcat   1980
ggaggctgcc cgcacctgct cccgcctgct cacaccctcc atccacctca tcagtggcca   2040
tgctcatgtg gttagccaga ccgcagtgca agtggtggca gatgtgctta gcaaactgct   2100
cgtagttggg ataacagatc ctgaccctga cattcgctac tgtgtcttgg cgtccctgga   2160
cgagcgcttt gatgcacacc tggcccaggc ggagaacttg caggccttgt ttgtggctct   2220
gaatgaccag gtgtttgaga tccgggagct ggccatctgc actgtgggcc gactcagtag   2280
catgaaccct gcctttgtca tgcctttcct gcgcaagatg ctcatccaga ttttgacaga   2340
gttggagcac agtgggattg gaagaatcaa agagcagagt gcccgcatgc tggggcacct   2400
ggtctccaat gccccccgac tcatccgccc ctacatggag cctattctga aggcattaat   2460
tttgaaactg aaagatccag accctgatcc aaacccaggt gtgatcaata atgtcctggc   2520
aacaatagga gaattggcac aggttagtgg cctggaaatg aggaaatggg ttgatgaact   2580
ttttattatc atcatggaca tgctccagga ttcctctttg ttggccaaaa ggcaggtggc   2640
tctgtggacc ctgggacagt tggtggccag cactggctat gtagtagagc cctacaggaa   2700
gtaccctact ttgcttgagg tgctactgaa ttttctgaag actgagcaga accagggtac   2760
acgcagagag gccatccgtg tgttagggct tttaggggct ttggatcctt acaagcacaa   2820
agtgaacatt ggcatgatag accagtcccg ggatgcctct gctgtcagcc tgtcagaatc   2880
caagtcaagt caggattcct ctgactatag cactagtgaa atgctggtca acatgggaaa   2940
cttgcctctg gatgagttct acccagctgt gtccatggtg gccctgatgc ggatcttccg   3000
agaccagtca ctctctcatc atcacaccat ggttgtccag gccatcacct tcatcttcaa   3060
gtccctggga ctcaaatgtg tgcagttcct gccccaggtc atgcccacgt tccttaacgt   3120
cattcgagtc tgtgatgggg ccatccggga atttttgttc cagcagctgg gaatgttggt   3180
gtcctttgtg aagagccaca tcagacctta tatggatgaa atagtcaccc tcatgagaga   3240
attctgggtc atgaacacct caattcagag cacgatcatt cttctcattg agcaaattgt   3300
ggtagctctt gggggtgaat ttaagctcta cctgccccag ctgatcccac acatgctgcg   3360
tgtcttcatg catgacaaca gcccaggccg cattgtctct atcaagttac tggctgcaat   3420
ccagctgttt ggcgccaacc tggatgacta cctgcattta ctgctgcctc ctattgttaa   3480
gttgtttgat gcccctgaag ctccactgcc atctcgaaag gcagcgctag agactgtgga   3540
ccgcctgacg gagtccctgg atttcactga ctatgcctcc cggatcattc accctattgt   3600
tcgaacactg gaccagagcc cagaactgcg ctccacagcc atggacacgc tgtcttcact   3660
tgtttttcag ctggggaaga agtaccaaat tttcattcca atggtgaata aagttctggt   3720
gcgacaccga atcaatcatc agcgctatga tgtgctcatc tgcagaattg tcaagggata   3780
cacacttgct gatgaagagg aggatccttt gatttaccag catcggatgc ttaggagtgg   3840
```

```
ccaaggggat gcattggcta gtggaccagt ggaaacagga cccatgaaga aactgcacgt   3900
cagcaccatc aacctccaaa aggcctgggg cgctgccagg agggtctcca aagatgactg   3960
gctggaatgg ctgagacggc tgagcctgga gctgctgaag gactcatcat cgccctccct   4020
gcgctcctgc tgggccctgg cacaggccta caacccgatg gccagggatc tcttcaatgc   4080
tgcatttgtg tcctgctggt ctgaactgaa tgaagatcaa caggatgagc tcatcagaag   4140
catcgagttg gccctcacct cacaagacat cgctgaagtc acacagaccc tcttaaactt   4200
ggctgaattc atggaacaca gtgacaaggg cccccctgcca ctgagagatg acaatggcat   4260
tgttctgctg ggtgagagag ctgccaagtg ccgagcatat gccaaagcac tacactacaa   4320
agaactggag ttccagaaag gccccacccc tgccattcta gaatctctca tcagcattaa   4380
taataagcta cagcagccgg aggcagcggc cggagtgtta gaatatgcca tgaaacactt   4440
tggagagctg gagatccagg ctacctggta tgagaaactg cacgagtggg aggatgccct   4500
tgtggcctat gacaagaaaa tggacaccaa caaggacgac ccagagctga tgctgggccg   4560
catgcgctgc ctcgaggcct tgggggaatg gggtcaactc caccagcagt gctgtgaaaa   4620
gtggaccctg gttaatgatg agacccaagc caagatggcc cggatggctg ctgcagctgc   4680
atggggttta ggtcagtggg acagcatgga agaatacacc tgtatgatcc ctcgggacac   4740
ccatgatggg gcattttata gagctgtgct ggcactgcat caggacctct tctccttggc   4800
acaacagtgc attgacaagg ccagggacct gctggatgct gaattaactg cgatggcagg   4860
agagagttac agtcgggcat atggggccat ggtttcttgc cacatgctgt ccgagctgga   4920
ggaggttatc cagtacaaac ttgtccccga gcgacgagag atcatccgcc agatctggtg   4980
ggagagactg cagggctgcc agcgtatcgt agaggactgg cagaaaatcc ttatggtgcg   5040
gtcccttgtg gtcagccctc atgaagacat gagaacctgg ctcaagtatg caagcctgtg   5100
cggcaagagt ggcaggctgg ctcttgctca taaaacttta gtgttgctcc tgggagttga   5160
tccgtctcgg caacttgacc atcctctgcc aacagttcac cctcaggtga cctatgccta   5220
catgaaaaac atgtggaaga gtgcccgcaa gatcgatgcc ttccagcaca tgcagcattt   5280
tgtccagacc atgcagcaac aggcccagca tgccatcgct actgaggacc agcagcataa   5340
gcaggaactg cacaagctca tggcccgatg cttcctgaaa cttggagagt ggcagctgaa   5400
tctacagggc atcaatgaga gcacaatccc caaagtgctg cagtactaca gcgccgccac   5460
agagcacgac cgcagctggt acaaggcctg gcatgcgtgg gcagtgatga acttcgaagc   5520
tgtgctacac tacaaacatc agaaccaagc ccgcgatgag aagaagaaac tgcgtcatgc   5580
cagcggggcc aacatcacca acgccaccac tgccgccacc acggccgcca ctgccaccac   5640
cactgccagc accgagggca gcaacagtga gagcgaggcc gagagcaccg agaacagccc   5700
caccccatcg ccgctgcaga agaaggtcac tgaggatctg tccaaaaccc tcctgatgta   5760
cacggtgcct gccgtccagg gcttcttccg ttccatctcc ttgtcacgag gcaacaacct   5820
ccaggataca ctcagagttc tcaccttatg gtttgattat ggtcactggc cagatgtcaa   5880
tgaggcctta gtggaggggg tgaaagccat ccagattgat acctggctac aggttatacc   5940
tcagctcatt gcaagaattg atacgcccag acccttggtg ggacgtctca ttcaccagct   6000
tctcacagac attggtcggt accacccccca ggccctcatc tacccactga cagtggcttc   6060
taagtctacc acgacagccc ggcacaatgc agccaacaag attctgaaga acatgtgtga   6120
gcacagcaac accctggtcc agcaggccat gatggtgagc gaggagctga tccgagtggc   6180
```

```
catcctctgg catgagatgt ggcatgaagg cctggaagag gcatctcgtt tgtactttgg   6240
ggaaaggaac gtgaaaggca tgtttgaggt gctggagccc ttgcatgcta tgatggaacg   6300
gggcccccag actctgaagg aaacatcctt taatcaggcc tatggtcgag atttaatgga   6360
ggcccaagag tggtgcagga agtacatgaa atcagggaat gtcaaggacc tcacccaagc   6420
ctgggacctc tattatcatg tgttccgacg aatctcaaag cagctgcctc agctcacatc   6480
cttagagctg caatatgttt ccccaaaact tctgatgtgc cgggaccttg aattggctgt   6540
gccaggaaca tatgacccca accagccaat cattcgcatt cagtccatag caccgtcttt   6600
gcaagtcatc acatccaagc agaggccccg gaaattgaca cttatgggca gcaacggaca   6660
tgagtttgtt ttccttctaa aaggccatga agatctgcgc caggatgagc gtgtgatgca   6720
gctcttcggc ctggttaaca cccttctggc caatgaccca acatctcttc ggaaaaacct   6780
cagcatccag agatacgctg tcatcccttt atcgaccaac tcgggcctca ttggctgggt   6840
tccccactgt gacacactgc acgccctcat ccgggactac agggagaaga agaagatcct   6900
tctcaacatc gagcatcgca tcatgttgcg gatggctccg gactatgacc acttgactct   6960
gatgcagaag gtggaggtgt ttgagcatgc cgtcaataat acagctgggg acgacctggc   7020
caagctgctg tggctgaaaa gccccagctc cgaggtgtgg tttgaccgaa gaaccaatta   7080
tacccgttct ttagcggtca tgtcaatggt tgggtatatt ttaggcctgg gagatagaca   7140
cccatccaac ctgatgctgg accgtctgag tgggaagatc ctgcacattg actttgggga   7200
ctgctttgag gttgctatga cccgagagaa gtttccagag aagattccat ttagactaac   7260
aagaatgttg accaatgcta tggaggttac aggcctggat ggcaactaca gaatcacatg   7320
ccacacagtg atggaggtgc tgcgagagca caaggacagt gtcatggccg tgctggaagc   7380
ctttgtctat gaccccttgc tgaactggag gctgatggac acaaatacca aaggcaacaa   7440
gcgatcccga acgaggacgg attcctactc tgctggccag tcagtcgaaa ttttggacgg   7500
tgtggaactt ggagagccag cccataagaa aacggggacc acagtgccag aatctattca   7560
ttctttcatt ggagacggtt tggtgaaacc agaggcccta aataagaaag ctatccagat   7620
tattaacagg gttcgagata agctcactgg tcgggacttc tctcatgatg acactttgga   7680
tgttccaacg caagttgagc tgctcatcaa acaagcgaca tcccatgaaa acctctgcca   7740
gtgctatatt ggctggtgcc ctttctggta actggaggcc cagatgtgcc catcacgttt   7800
tttctgaggc ttttgtactt tagtaaatgc ttccactaaa ctgaaaccat ggtgagaaag   7860
tttgactttg ttaaatattt tgaaatgtaa atgaaaagaa ctactgtata ttaaaagttg   7920
gtttgaacca actttctagc tgctgttgaa gaatatattg tcagaaacac aaggcttgat   7980
ttggttccca ggacagtgaa acatagtaat accacgtaaa tcaagccatt cattttgggg   8040
aacagaagat ccataacttt agaaatacgg gttttgactt aactcacaag agaactcatc   8100
ataagtactt gctgatggaa gaatgaccta gttgctcctc tcaacatggg tacagcaaac   8160
tcagcacagc caagaagcct caggtcgtgg agaacatgga ttaggatcct agactgtaaa   8220
gacacagaag atgctgacct cacccctgcc acctatccca agacctcact ggtctgtgga   8280
cagcagcaga aatgtttgca agataggcca aaatgagtac aaaaggtctg tcttccatca   8340
gacccagtga tgctgcgact cacacgcttc aattcaagac ctgaccgcta gtagggaggt   8400
ttattcagat cgctggcagc ctcggctgag cagatgcaca gaggggatca ctgtgcagtg   8460
ggaccaccct cactggcctt ctgcagcagg gttctgggat gttttcagtg gtcaaaatac   8520
tctgtttaga gcaagggctc agaaaacaga aatactgtca tggaggtgct gaacacaggg   8580
```

aaggtctggt acatattgga aattatgagc agaacaaata ctcaactaaa tgcacaaagt 8640
ataaagtgta gccatgtcta gacaccatgt tgtatcagaa taatttttgt gccaataaat 8700
gacatcagaa ttttaaacat atgtaaaaaa aaa 8733

<210> SEQ ID NO 8
<211> LENGTH: 19
<212> TYPE: DNA
<213> ORGANISM: Artificial Sequence
<220> FEATURE:
<223> OTHER INFORMATION: Primer

<400> SEQUENCE: 8
cattcgggcc gagatgtct 19

<210> SEQ ID NO 9
<211> LENGTH: 24
<212> TYPE: DNA
<213> ORGANISM: Artificial Sequence
<220> FEATURE:
<223> OTHER INFORMATION: Primer

<400> SEQUENCE: 9
ctccaggcca gaaagagaga gtag 24

<210> SEQ ID NO 10
<211> LENGTH: 22
<212> TYPE: DNA
<213> ORGANISM: Artificial Sequence
<220> FEATURE:
<223> OTHER INFORMATION: Probe

<400> SEQUENCE: 10
ccgtggcctt agctgtgctc gc 22

<210> SEQ ID NO 11
<211> LENGTH: 21
<212> TYPE: DNA
<213> ORGANISM: Artificial Sequence
<220> FEATURE:
<223> OTHER INFORMATION: Primer

<400> SEQUENCE: 11
cacatggcct ccaaggagta a 21

<210> SEQ ID NO 12
<211> LENGTH: 24
<212> TYPE: DNA
<213> ORGANISM: Artificial Sequence
<220> FEATURE:
<223> OTHER INFORMATION: Primer

<400> SEQUENCE: 12
tgagggtctc tctcttcctc ttgt 24

<210> SEQ ID NO 13
<211> LENGTH: 22
<212> TYPE: DNA
<213> ORGANISM: Artificial Sequence
<220> FEATURE:
<223> OTHER INFORMATION: Probe

<400> SEQUENCE: 13
ctggaccacc agccccagca ag 22

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
ccagggattt gcctcacctt 20

<210> SEQ ID NO 15
<211> LENGTH: 21
<212> TYPE: DNA
<213> ORGANISM: Artificial Sequence
<220> FEATURE:
<223> OTHER INFORMATION: Primer

<400> SEQUENCE: 15
aaagagatga agcccccaca t 21

<210> SEQ ID NO 16
<211> LENGTH: 26
<212> TYPE: DNA
<213> ORGANISM: Artificial Sequence
<220> FEATURE:
<223> OTHER INFORMATION: Probe

<400> SEQUENCE: 16
ccttgatgac tgccttgcct cctcag 26

<210> SEQ ID NO 17
<211> LENGTH: 23
<212> TYPE: DNA
<213> ORGANISM: Artificial Sequence
<220> FEATURE:
<223> OTHER INFORMATION: Primer

<400> SEQUENCE: 17
gctcgagatg tgatgaagga gat 23

<210> SEQ ID NO 18
<211> LENGTH: 21
<212> TYPE: DNA
<213> ORGANISM: Artificial Sequence
<220> FEATURE:
<223> OTHER INFORMATION: Primer

<400> SEQUENCE: 18
ccagcaggtc agcaaagaat t 21

<210> SEQ ID NO 19
<211> LENGTH: 28
<212> TYPE: DNA
<213> ORGANISM: Artificial Sequence
<220> FEATURE:
<223> OTHER INFORMATION: Probe

<400> SEQUENCE: 19
ccatcacatt gtagccctct gtgtgctc 28

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20
cacctagtgg ctgggagctt 20

<210> SEQ ID NO 21
<211> LENGTH: 24
<212> TYPE: DNA
<213> ORGANISM: Artificial Sequence
<220> FEATURE:
<223> OTHER INFORMATION: Primer

<400> SEQUENCE: 21
gcccagtttt atcatctcac aaga 24

<210> SEQ ID NO 22
<211> LENGTH: 27
<212> TYPE: DNA
<213> ORGANISM: Artificial Sequence
<220> FEATURE:
<223> OTHER INFORMATION: Probe

<400> SEQUENCE: 22
tggcacttac ctttgtccct tgcttca 27

<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23
gaaggagctg cccatgagaa 20

<210> SEQ ID NO 24
<211> LENGTH: 21
<212> TYPE: DNA
<213> ORGANISM: Artificial Sequence
<220> FEATURE:
<223> OTHER INFORMATION: Primer

<400> SEQUENCE: 24
gactatgtcc cgccactgga t 21

<210> SEQ ID NO 25
<211> LENGTH: 21
<212> TYPE: DNA
<213> ORGANISM: Artificial Sequence
<220> FEATURE:
<223> OTHER INFORMATION: Probe

<400> SEQUENCE: 25
aaatcctgca tggcgccgtg c 21

<210> SEQ ID NO 26
<211> LENGTH: 23
<212> TYPE: DNA
<213> ORGANISM: Artificial Sequence
<220> FEATURE:
<223> OTHER INFORMATION: Primer

<400> SEQUENCE: 26
caccactcaa acgctgacat gta 23

<210> SEQ ID NO 27

<211> LENGTH: 22
<212> TYPE: DNA
<213> ORGANISM: Artificial Sequence
<220> FEATURE:
<223> OTHER INFORMATION: Primer

<400> SEQUENCE: 27
ccaactgcca ataccagtgg at 22

<210> SEQ ID NO 28
<211> LENGTH: 23
<212> TYPE: DNA
<213> ORGANISM: Artificial Sequence
<220> FEATURE:
<223> OTHER INFORMATION: Probe

<400> SEQUENCE: 28
tatgccattc ctcccccgca tca 23

<210> SEQ ID NO 29
<211> LENGTH: 16
<212> TYPE: DNA
<213> ORGANISM: Artificial Sequence
<220> FEATURE:
<223> OTHER INFORMATION: Primer

<400> SEQUENCE: 29
agcgctggcg aaatcg 16

<210> SEQ ID NO 30
<211> LENGTH: 19
<212> TYPE: DNA
<213> ORGANISM: Artificial Sequence
<220> FEATURE:
<223> OTHER INFORMATION: Primer

<400> SEQUENCE: 30
ttcacgcgaa ccagtgtca 19

<210> SEQ ID NO 31
<211> LENGTH: 21
<212> TYPE: DNA
<213> ORGANISM: Artificial Sequence
<220> FEATURE:
<223> OTHER INFORMATION: Probe

<400> SEQUENCE: 31
ctgtccacgc gcaacgtgtc g 21

<210> SEQ ID NO 32
<211> LENGTH: 20
<212> TYPE: DNA
<213> ORGANISM: Artificial Sequence
<220> FEATURE:
<223> OTHER INFORMATION: Primer

<400> SEQUENCE: 32
cacgggacat tcaccacatc 20

<210> SEQ ID NO 33
<211> LENGTH: 19
<212> TYPE: DNA
<213> ORGANISM: Artificial Sequence
<220> FEATURE:
<223> OTHER INFORMATION: Primer

<400> SEQUENCE: 33
gggtgccatc cacttcaca 19

<210> SEQ ID NO 34
<211> LENGTH: 30
<212> TYPE: DNA
<213> ORGANISM: Artificial Sequence
<220> FEATURE:
<223> OTHER INFORMATION: Probe

<400> SEQUENCE: 34
actataaaaa gacaaccaac ggccgactgc 30

<210> SEQ ID NO 35
<211> LENGTH: 21
<212> TYPE: DNA
<213> ORGANISM: Artificial Sequence
<220> FEATURE:
<223> OTHER INFORMATION: Primer

<400> SEQUENCE: 35
aggccgcatt gtctctatca a 21

<210> SEQ ID NO 36
<211> LENGTH: 24
<212> TYPE: DNA
<213> ORGANISM: Artificial Sequence
<220> FEATURE:
<223> OTHER INFORMATION: Primer

<400> SEQUENCE: 36
gcagtaaatg caggtagtca tcca 24

<210> SEQ ID NO 37
<211> LENGTH: 22
<212> TYPE: DNA
<213> ORGANISM: Artificial Sequence
<220> FEATURE:
<223> OTHER INFORMATION: Probe

<400> SEQUENCE: 37
tgcaatccag ctgtttggcg cc 22

<210> SEQ ID NO 38
<211> LENGTH: 23
<212> TYPE: DNA
<213> ORGANISM: Artificial Sequence
<220> FEATURE:
<223> OTHER INFORMATION: Primer

<400> SEQUENCE: 38
gaggtcgaca tccacaccta atg 23

<210> SEQ ID NO 39
<211> LENGTH: 22
<212> TYPE: DNA
<213> ORGANISM: Artificial Sequence
<220> FEATURE:
<223> OTHER INFORMATION: Primer

<400> SEQUENCE: 39
tcgaattgca tcctcaatca tc 22

<210> SEQ ID NO 40
<211> LENGTH: 23
<212> TYPE: DNA

-continued

```
<213> ORGANISM: Artificial Sequence
<220> FEATURE:
<223> OTHER INFORMATION: Probe

<400> SEQUENCE: 40

ccacatggtc agcaccaccc tgc                                              23


<210> SEQ ID NO 41
<211> LENGTH: 23
<212> TYPE: DNA
<213> ORGANISM: Artificial Sequence
<220> FEATURE:
<223> OTHER INFORMATION: Primer

<400> SEQUENCE: 41

cagatttcag agagcaccaa tca                                              23


<210> SEQ ID NO 42
<211> LENGTH: 21
<212> TYPE: DNA
<213> ORGANISM: Artificial Sequence
<220> FEATURE:
<223> OTHER INFORMATION: Primer

<400> SEQUENCE: 42

aatggtctac cacgggcttc t                                                21


<210> SEQ ID NO 43
<211> LENGTH: 30
<212> TYPE: DNA
<213> ORGANISM: Artificial Sequence
<220> FEATURE:
<223> OTHER INFORMATION: Probe

<400> SEQUENCE: 43

ttactccaac ttagcaaact gcagccccaa                                       30
```

ANALYTICAL METHOD FOR INCREASING SUSCEPTIBILITY OF MOLECULAR TARGETED THERAPY IN HEPATOCELLULAR CARCINOMA

"The Sequence Listing submitted in text format (.txt) filed on Jul. 31, 2015, named "SequenceListing.TXT", created on Jul. 6, 2015, 57.4 KB), is incorporated herein by reference."

TECHNICAL FIELD

The present invention relates to an analytical method for increasing susceptibility of molecular targeted therapy in hepatocellular carcinoma. More specifically, the present invention relates to an analytical method for determining whether a hepatocellular carcinoma patient has susceptibility or resistance to sorafenib treatment.

BACKGROUND ART

Hepatocellular carcinoma (HCC) is the most common primary liver malignancy. HCC is the sixth most common cancer and the third most common cause of cancer mortality in the world (Yang J D, et al., (2010) *Nat Rev Gastroenterol Hepatol* 7: 314 448-458). Many molecular targeted drugs have entered clinical trials as palliative and adjuvant treatments for HCC (Villanueva A, et al., (2011) *Gastroenterology* 140: 316 1410-1426). The multikinase inhibitor sorafenib was approved for the first-line therapy in advanced HCC as a result of a statistically significant but modest improvement of overall survival and time to progression in two randomized controlled trials (Llovet J M, et al., (2008) *N Engl J Med* 359: 378-390 and Cheng A L, et al., (2009) *Lancet Oncol* 10: 25-34). Other molecular targeted drugs have been tested in combination with sorafenib or in the adjuvant setting (Zhu A X (2012), *Semin Oncol* 39: 493-502. and Huynh H (2010) *Biochem Pharmacol* 80: 550-560). However, it is well-known in the art that the benefits of current molecular targeted agents including sorafenib are very limited. The response rate in the phase III clinical trial using sorafenib is very low, i.e., only 2.3% to 3.30% (Villanueva A, et al., (2012) *Clin Cancer Res* 18: 1824-1826).

Biomarkers are increasingly used for diagnosis, prognosis, and therapeutic decision making in diverse cancers, propelling a paradigm shift in the management of cancer. Biomarkers have helped to stratify patients and thus achieve better outcomes from a given drug in the clinic Trastuzumab, a HER2 targeting monoclonal antibody, is effective in metastatic breast cancer patients with 3+ HER2 over-expression assessed by immunohistochemistry (IHC) or HER2 gene amplification (Vogel C L, et al., (2002) *J Clin Oncol* 20: 719-726). Also, patients with non-small cell lung cancer harboring activating mutations within the kinase domain of EGFR show impressive clinical responses to the EGFR inhibitor gefitinib (Lynch T J, et al., *N Engl J Med* 350: 2129-2139). This type of molecular classification which stratifies individual tumors into molecular subtypes for which targeted therapy could have potential efficacy is described as actionable molecular subtyping (West L, et al., PLoS One 7: e31906. and Vidwans S J, et al., PLoS One 6: e18257).

DISCLOSURE OF INVENTION

Technical Problem

The present inventors have found that the stratification of HCC patients by cluster analysis of mRNA expression of specific genes, i.e., VEGFR2, PDGFRβ, c-KIT, EGFR, c-RAF, mTOR, and FGFR1, as biomarkers makes it possible to select a patient having susceptibility to the treatment with sorafenib, one of the molecular targeted agents. Especially, it has been newly found that FGFR1 has relationship with susceptibility to sorafenib treatment. Therefore, the analysis on the mRNA expression of FGFR1, optionally along with the mRNA expression of other biomarkers (i.e., VEGFR2, PDGFRβ, c-KIT, c-RAF, EGFR, and/or mTOR), makes it possible to select a patient having susceptibility to sorafenib treatment and a patient having resistance to sorafenib treatment before employing molecular targeted therapy with sorafenib.

Therefore, it is an object of the present invention to provide an analytical method for determining whether a hepatocellular carcinoma patient has susceptibility or resistance to sorafenib treatment, which involves using FGFR1 as a biomarker or using VEGFR2, PDGFRβ, c-KIT, c-RAF, EGFR, and/or mTOR along with FGFR1 as biomarkers.

Solution to Problem

In accordance with an aspect of the present invention, there is provided an analytical method for determining whether a hepatocellular carcinoma patient has susceptibility or resistance to sorafenib treatment, the method of which comprises: (i) measuring mRNA expression levels of the gene of SEQ ID NO: 1 in both hepatocellular carcinoma tissues and normal tissues, which are externally discharged from the hepatocellular carcinoma patient, and (ii) measuring a ratio between the mRNA expression level of the gene of SEQ ID NO: 1 in the hepatocellular carcinoma tissues and the mRNA expression level of the gene of SEQ ID NO: 1 in the normal tissues.

In an embodiment, there is provided the analytical method for determining whether a hepatocellular carcinoma patient has susceptibility or resistance to sorafenib treatment, which comprises: (i') measuring mRNA expression levels of the gene of SEQ ID NO: 1 and mRNA expression levels of one or more genes selected from the group consisting of SEQ ID NOs: 2 to 7 in both hepatocellular carcinoma tissues and normal tissues, which are externally discharged from the hepatocellular carcinoma patient, and (ii') measuring the ratio between the mRNA expression level of the gene of SEQ ID NO: 1 in the hepatocellular carcinoma tissues and the mRNA expression level of the gene of SEQ ID NO: 1 in the normal tissues; and a ratio between the mRNA expression levels of one or more genes selected from the group consisting of SEQ ID NOs: 2 to 7 in the hepatocellular carcinoma tissues and the mRNA expression levels of one or more genes selected from the group consisting of SEQ ID NOs: 2 to 7 in the normal tissues.

In another embodiment, there is provided the analytical method for determining whether a hepatocellular carcinoma patient has susceptibility or resistance to sorafenib treatment, which comprises: (i") measuring mRNA expression levels of the genes of SEQ ID NOs: 1, 3, 4, 6, and 7 in both hepatocellular carcinoma tissues and normal tissues, which are externally discharged from the hepatocellular carcinoma patient, and (ii") measuring the ratio between the mRNA expression level of the genes of SEQ ID NOs: 1, 3, 4, 6, and 7 in the hepatocellular carcinoma tissues and the mRNA expression level of the genes of SEQ ID NOs: 1, 3, 4, 6, and 7 in the normal tissues.

In still another embodiment, there is provided an analytical method for determining whether a hepatocellular carcinoma patient has susceptibility or resistance to sorafenib treatment, the method of which comprises: (i''') measuring mRNA expression levels of the genes of SEQ ID NOs: 1 to 7 in hepatocellular carcinoma tissues, which are externally discharged from the hepatocellular carcinoma patient, and (ii''') calculating the sum of the mRNA expression levels.

In the analytical method of the present invention, the mRNA expression level may be measured by real-time reverse transcriptase-polymerase chain reaction.

Advantageous Effects of Invention

It has been found by the present invention that the stratification of HCC patients by cluster analysis of mRNA expression of specific genes, i.e., VEGFR2, PDGFRβ, c-KIT, EGFR, c-RAF, mTOR, and FGFR1, as biomarkers makes it possible to select patients having susceptibility to the treatment with sorafenib, one of the molecular targeted agents. In addition, it has been found by the present invention that a patient having susceptibility to sorafenib treatment can be selected by an analysis using only the tumor tissues, the analysis of which involves using the sum of the expression levels of said 7 marker genes. Especially, it has been newly found that FGFR1 has relationship with susceptibility to sorafenib treatment. Therefore, the analysis on the mRNA expression of FGFR1, optionally along with the mRNA expression of other biomarkers (i.e., VEGFR2, PDGFRβ, c-KIT, c-RAF, EGFR, and/or mTOR), makes it possible to select a patient having susceptibility to sorafenib treatment.

BRIEF DESCRIPTION OF DRAWINGS

FIG. 1 shows the frequency of mRNA over-expressions of 4 marker genes (VEGFR2, PDGFRβ, c-KIT, c-RAF), which are known as genes associated with the efficacy of sorafenib, in 130 HCC and matched non-tumor tissues.

FIG. 2 shows the expression levels of marker genes in matched non-tumor tissues and tumor tissues according to BCLC stages (A: Early, B: intermediate, C: Advanced). In FIG. 2, A to G respectively show the expression levels of VEGFR2 (A); PDGFRβ (B); c-KIT (C); c-RAF (D); EGFR (E); mTOR (F); and FGFR1 (G).

FIG. 3 shows the frequency of over-expression in tumor tissues compared to matched non-tumor tissues, through measuring the expression levels of 7 marker genes in tissues derived from paired 130 HCC patients.

FIG. 4 shows the frequency of over-expression in tumor tissues compared to non-tumor tissues according to the BCLC stages, through measuring the expression levels of 7 marker genes in tissues derived from paired 130 HCC patients.

FIG. 5 shows the results of hierarchical clustering analyses according to marker gene expression patterns for clustering the patients.

FIG. 6 shows the relationship between the marker gene expression patterns and the sorafenib efficacies, in the samples derived from 23 sorafenib-administered patients.

FIG. 7 shows the interactive dot diagram of NTBS values obtained from 23 sorafenib-administered patients (A); and the ROC (receiver operating characteristic) curve obtained therefrom (B).

BEST MODE FOR CARRYING OUT THE INVENTION

As used herein, the term "sorafenib" refers to the compound of the following Formula 1, including its pharmaceutically acceptable salt, for example p-toluenesulfonate salt.

⟨Formula 1⟩

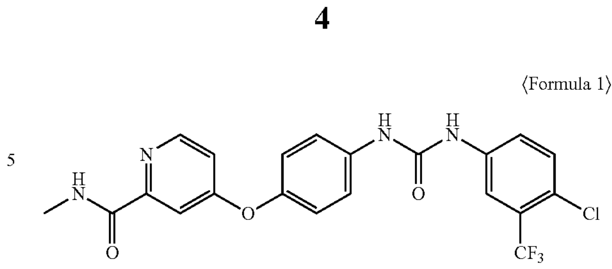

The term "patient having susceptibility to sorafenib treatment" refers to a hepatocellular carcinoma patient showing response according to the sorafenib administration (i.e., tumor response). The "tumor response" refers to complete response, partial response, or stable disease according to the RECIST (Response Evaluation Criteria in Solid Tumors) defined in Llovet J M, et al. (2008) Sorafenib in advanced hepatocellular carcinoma. *N Engl J Med* 359: 378-390.

The term "hepatocellular carcinoma tissues" and "normal tissues" refer to the tissues samples externally discharged, via e.g., biopsy, from the hepatocellular carcinoma tissues and the surrounding non-tumor tissues derived from a hepatocellular carcinoma patient. In clinics, carcinoma tissues and surrounding normal tissues are generally collected from a patient and then tissue examinations thereof are carried out for diagnosing hepatocellular carcinoma and/or establishing therapeutic regimen. Therefore, the term "hepatocellular carcinoma tissues" and "normal tissues" refer to the tissues samples externally discharged from a patient, e.g., for tissue examination in clinics.

In order to improve very low response rate of sorafenib (about 3%), the present inventors carried out analyses on the expression patterns of various target biomarkers in tissue samples derived from HCC patients, including hierarchical clustering analyses. As a result thereof, it has been surprisingly found by the present invention that FGFR1 has relationship with susceptibility to sorafenib treatment, which was not reported in the previous literatures. That is, it has been newly found that a patient showing the mRNA expression level of the FGFR1 gene (the gene of SEQ ID NO: 1) lower in the tumor tissues than in the normal tissues has high resistance to sorafenib treatment, thereby exhibiting significantly low therapeutic efficacy. Therefore, through analyzing a ratio between the mRNA expression of FGFR1 (the gene of SEQ ID NO: 1) in normal tissues and the mRNA expression of FGFR1 (the gene of SEQ ID NO: 1) in hepatocellular carcinoma tissues, patient having susceptibility or resistance to sorafenib treatment can be selected in advance; and thus the response rate to sorafenib treatment can be remarkably increased.

Therefore, the present invention provides an analytical method for determining whether a hepatocellular carcinoma patient has susceptibility or resistance to sorafenib treatment, the method of which comprises: (i) measuring mRNA expression levels of the gene of SEQ ID NO: 1 in both hepatocellular carcinoma tissues and normal tissues, which are externally discharged from the hepatocellular carcinoma patient, and (ii) measuring a ratio between the mRNA expression level of the gene of SEQ ID NO: 1 in the hepatocellular carcinoma tissues and the mRNA expression level of the gene of SEQ ID NO: 1 in the normal tissues. In the analytical method of the present invention, if the T/N ratio (tumor/non-tumor ratio) of the mRNA expression level of the gene of SEQ ID NO: 1 in hepatocellular carcinoma tissues to the mRNA expression level of the gene of SEQ ID NO: 1 in normal tissues is more than 2, the patient can be classified to a patient having low resistance to sorafenib treatment, i.e., a patient having high susceptibility to sorafenib treatment.

And also, the present inventors carried out hierarchical clustering analyses on VEGFR2 (the gene of SEQ ID NO: 2), PDGFRβ (the gene of SEQ ID NO: 3), c-KIT (the gene of SEQ ID NO: 4), c-RAF (the gene of SEQ ID NO: 5), EGFR (the gene of SEQ ID NO: 6), and mTOR (the gene of SEQ ID NO: 7), in addition to FGFR1 (the gene of SEQ ID NO: 1). As a result thereof, it has been found that the analyses on such genes along with FGFR1 (the gene of SEQ ID NO: 1) make it possible to select hepatocellular carcinoma patients having susceptibility to sorafenib treatment in higher efficiency. Therefore, in an embodiment, the present invention provides an analytical method for determining whether a hepatocellular carcinoma patient has susceptibility or resistance to sorafenib treatment, which comprises: (i') measuring mRNA expression levels of the gene of SEQ ID NO: 1 and mRNA expression levels of one or more genes selected from the group consisting of SEQ ID NOs: 2 to 7 in both hepatocellular carcinoma tissues and normal tissues, which are externally discharged from the hepatocellular carcinoma patient, and (ii') measuring the ratio between the mRNA expression level of the gene of SEQ ID NO: 1 in the hepatocellular carcinoma tissues and the mRNA expression level of the gene of SEQ ID NO: 1 in the normal tissues; and a ratio between the mRNA expression levels of one or more genes selected from the group consisting of SEQ ID NOs: 2 to 7 in the hepatocellular carcinoma tissues and the mRNA expression levels of one or more genes selected from the group consisting of SEQ ID NOs: 2 to 7 in the normal tissues. In said embodiment, if (1) the T/N ratio (tumor/non-tumor ratio) of the mRNA expression level of the gene of SEQ ID NO: 1 in hepatocellular carcinoma tissues to the mRNA expression level of the gene of SEQ ID NO: 1 in normal tissues is more than 2; (2) the T/N ratio(s) of the mRNA expression level(s) of one or more genes selected from the group consisting of SEQ ID NOs: 2 to 5 in hepatocellular carcinoma tissues to the mRNA expression level(s) of one or more genes selected from the group consisting of SEQ ID NOs: 2 to 5 in normal tissues is more than 2; and (3) the T/N ratio(s) of the mRNA expression level(s) of one or more genes of SEQ ID NOs: 6 to 7 in hepatocellular carcinoma tissues to the mRNA expression level(s) of one or more genes selected from the group consisting of SEQ ID NOs: 6 to 7 in normal tissues is less than 2, the patient can be classified to a patient having low resistance to sorafenib treatment, i.e., a patient having high susceptibility to sorafenib treatment.

And also, it has been found that the genes of SEQ ID NOs: 3, 4, 6, and 7, among the genes of SEQ ID NOs: 2 to 7, are more preferable as genes for being analyzed in combination with the gene of SEQ ID NO: 1. Therefore, in another embodiment, the present invention provides an analytical method for determining whether a hepatocellular carcinoma patient has susceptibility or resistance to sorafenib treatment, which comprises: (i") measuring mRNA expression levels of the genes of SEQ ID NOs: 1, 3, 4, 6, and 7 in both hepatocellular carcinoma tissues and normal tissues, which are externally discharged from the hepatocellular carcinoma patient, and (ii") measuring the ratio between the mRNA expression level of the genes of SEQ ID NOs: 3, 4, 6, and 7 in the hepatocellular carcinoma tissues and the mRNA expression level of the genes of SEQ ID NOs: 1, 3, 4, 6, and 7 in the normal tissues. In said embodiment, if (1) the T/N ratio of the mRNA expression level of the gene of SEQ ID NO: 1 in hepatocellular carcinoma tissues to the mRNA expression level of the gene of SEQ ID NO: 1 in normal tissues is more than 2; (2) the T/N ratios of the mRNA expression levels of the genes of SEQ ID NOs: 3 and 4 in hepatocellular carcinoma tissues to the mRNA expression levels of the genes of SEQ ID NOs: 3 and 4 in normal tissues is more than 2; and (3) the T/N ratio of the mRNA expression level of the gene of SEQ ID NO: 6 and 7 in hepatocellular carcinoma tissues to the mRNA expression level of the gene of SEQ ID NO: 6 and 7 in normal tissues is less than 2, the patient can be classified to a patient having low resistance to sorafenib treatment, i.e., a patient having high susceptibility to sorafenib treatment.

In addition, it has been found that a patient having susceptibility to sorafenib treatment can be selected by an analysis using only the tumor tissues, the analysis of which involves using a new parameter, i.e., NTBS (Nexavar Treatment Benefit Score). The NTBS refers to the sum of the expression levels of said 7 marker genes. That is, the NTBS value refers to the sum of each mRNA expression level ($2^{-\Delta CT}$) of the marker genes of SEQ ID NOs: 1 to 7. Therefore, in still another embodiment, the present invention provides an analytical method for determining whether a hepatocellular carcinoma patient has susceptibility or resistance to sorafenib treatment, which comprises: (i'") measuring mRNA expression levels of the genes of SEQ ID NOs: 1 to 7 in hepatocellular carcinoma tissues, which are externally discharged from the hepatocellular carcinoma patient, and (ii'") calculating the sum of the mRNA expression levels. In said embodiment, if the sum of all the mRNA expression levels of the genes of SEQ ID NOs: 1 to 7 in hepatocellular carcinoma tissues (i.e., NTBS value) is more than a threshold value (e.g., 0.0758), preferably more than 0.1, the patient can be classified to a patient having susceptibility to sorafenib treatment.

In the analytical method of the present invention, the mRNA expression level may be measured according to conventional methods used in the field of biotechnology, for example, according to real-time reverse transcriptase-polymerase chain reaction (real-time RT-PCR). The real-time RT-PCR may be performed with an appropriate primer set for each gene. The primer set may be a known primer set; or prepared according to conventional methods.

The present invention will be described in further detail with reference to the following examples. These examples are for illustrative purposes only and are not intended to limit the scope of the present invention.

1. Test Methods (1) Patients, Materials and Methods

Hepatocellular carcinoma (HCC) tissues and corresponding non-cancerous hepatic tissues were obtained with informed consent from 130 patients who had undergone curative resection for primary HCC between 1998 and 2006 at the Ajou and Samsung Medical Centers in South Korea. The study protocol was approved by the Institutional Review Board of each Medical Center. Table 1 summarizes the demographic characteristics of the 130 HCC patients investigated in the current study. The present inventors used BCLC stage and Edmondson and Steiner grade according to the published criteria (Forner A, et al., (2010) *Semin Liver Dis* 30: 61-74. 346; and Edmondson H A, et al., (1954) *Cancer* 7: 462-503).

TABLE 1

| Variables | Charac-teristics | Number | Variables | Charac-teristics | Number |
|---|---|---|---|---|---|
| Age | <55 years | 80 | Child-Pugh | A | 126 |
| | ≥55 years | 50 | class | B | 4 |
| Gender | Male | 97 | | C | 0 |
| | Female | 33 | BCLC stage | A | 74 |
| HBV | Absent | 30 | | B | 39 |
| | Present | 100 | | C | 17 |
| HCV | Absent | 118 | Vascular | Absent | 57 |
| | Present | 12 | invasion | Present | 73 |
| Liver | Absent | 69 | Tumor number | Single | 104 |
| cirrhosis$^{-1}$ | Present | 60 | | Multiple | 26 |
| AFP level | <100 ng/mL | 75 | Tumor size | ≤5 cm | 93 |
| | ≥100 ng/mL | 55 | | >5 cm | 37 |
| Tumor | I | 55 | Edmondson | I | 18 |
| stage | II | 49 | grade | II | 95 |
| | III | 25 | | III | 17 |
| | IV | 1 | | IV | 0 |

* minus values mean the number of patients without the relevant clinicopathology information <2> RNA Extraction, cDNA Synthesis, and Real-Time RT-PCR Total RNAs were extracted from the HCC tissues and the surrounding normal tissues with RNeasy Mini kit (Qiagen, Germany) according to the vendor's instruction. The resulting total RNA extracts were subject to quantitative analysis using Bioanalyzer 2100 (Agilent Technologies, USA). During the extraction, contaminants (i.e., genome DNAs) were removed by treating the RNA extracts with DNase I. Each total RNA (4 μg) was reacted with 2 μl of 1 μM oligo d(T) 18 primer (Genotech, Korea) at 70° C. for 7 minutes and then cooled over ice for 5 minutes. An enzyme mixture [0.1 M DTT (Duchefa, Nethelands) 2 μl, 10× reverse transcriptase buffer 2 μl, 2 mM dNTP 5 μl, 200 U/μl MMLV reverse transcriptase 1 μl, and 40 U/μl RNase inhibitor (Enzynomics, Korea) 1 μl; total 11 μl] was separately prepared. The enzyme mixture was added to the RNA-containing mixture. The resulting mixture was incubated at 42° C. for 90 minutes and then at 80° C. for 10 minutes to inactivate the reverse transcriptase. Diethyl pyrocarbonate (DEPC)-treated water was added to the mixture to obtain a cDNA-containing solution having 400 μl of the final volume. The resulting solution was used for quantitative real time RT-PCR.

Real-time RT-PCR was carried out as described previously (Kwon J H, et al., (2010) *Clin Cancer Res* 16: 350 5511-5521). Briefly, the each cDNA sample was subject to real time RT-PCR on the gene marker, using PRISM 7900HT (Applied Biosystems, USA) according to the vendor's instruction. Real-time RT-PCR was performed with a solution (10 μl in total) containing 2× TaqMan Gene Expression Master Mix (Applied Biosystems, USA) 5 μl, 5 μM sense primer 1 μl, 5 μM antisense primer 1 μl, 1 μM probe (Genotech, Korea) 1 μl, cDNA 2 μl (in case of the control group, the same volume of water). After the initial denaturation at 95° C. for 10 minutes, the amplification was carried out in the cycle of denaturation at 95° C. for 15 seconds and extension at 60° C. for 1 minute. The primers and probes were prepared using Primer Express 3.0 (Applied Biosystems, USA) and then labeled with FAM and TAMRA at the 5' end and 3' end, respectively. The expressions of each marker gene were measured in triplicate and then normalized to 5 reference genes (B2M, GAPDH, HMBS, HPRT1, and SDHA) by subtracting the average values of the mRNA levels of the reference genes. The CTs (number of cycles for attaining to the threshold) of each marker gene were measured. From the ΔCT values (CT of the marker gene—average CT of reference genes), the mRNA expression levels thereof were calculated as $2^{-\Delta CT}$. The primers and probes of each marker gene are shown in Table 2 below.

TABLE 2

| Gene | | Sequence | SEQ ID |
|---|---|---|---|
| B2M | F | CATTCGGGCCGAGATGTCT | 8 |
| | R | CTCCAGGCCAGAAAGAGAGAGTAG | 9 |
| | P | CCGTGGCCTTAGCTGTGCTCGC | 10 |
| GAPDH | F | CACATGGCCTCCAAGGAGTAA | 11 |
| | R | TGAGGGTCTCTCTCTTCCTCTTGT | 12 |
| | P | CTGGACCACCAGCCCCAGCAAG | 13 |
| HMBS | F | CCAGGGATTTGCCTCACCTT | 14 |
| | R | AAAGAGATGAAGCCCCCACAT | 15 |
| | P | CCTTGATGACTGCCTTGCCTCCTCAG | 16 |
| HPRT1 | F | GCTCGAGATGTGATGAAGGAGAT | 17 |
| | R | CCAGCAGGTCAGCAAAGAATT | 18 |
| | P | CCATCACATTGTAGCCCTCTGTGTGCTC | 19 |
| SDHA | F | CACCTAGTGGCTGGGAGCTT | 20 |
| | R | GCCCAGTTTTATCATCTCACAAGA | 21 |
| | P | TGGCACTTACCTTTGTCCCTTGCTTCA | 22 |
| EGFR | F | GAAGGAGCTGCCCATGAGAA | 23 |
| | R | GACTATGTCCCGCCACTGGAT | 24 |
| | P | AAATCCTGCATGGCGCCGTGC | 25 |
| VEGFR2 | F | CACCACTCAAACGCTGACATGTA | 26 |
| | R | CCAACTGCCAATACCAGTGGAT | 27 |
| | P | TATGCCATTCCTCCCCCGCATCA | 28 |
| PDGFRβ | F | AGCGCTGGCGAAATCG | 29 |
| | R | TTCACGCGAACCAGTGTCA | 30 |
| | P | CTGTCCACGCGCAACGTGTCG | 31 |
| FGFR1 | F | CACGGGACATTCACCACATC | 32 |
| | R | GGGTGCCATCCACTTCACA | 33 |
| | P | ACTATAAAAAGACAACCAACGGCCGACTGC | 34 |
| mTOR | F | AGGCCGCATTGTCTCTATCAA | 35 |
| | R | GCAGTAAATGCAGGTAGTCATCCA | 36 |
| | P | TGCAATCCAGCTGTTTGGCGCC | 37 |
| C-RAF | F | GAGGTCGACATCCACACCTAATG | 38 |
| | R | TCGAATTGCATCCTCAATCATC | 39 |
| | P | CCACATGGTCAGCACCACCCTGC | 40 |
| C-KIT | F | CAGATTTCAGAGAGCACCAATCA | 41 |
| | R | AATGGTCTACCACGGGCTTCT | 42 |
| | P | TTACTCCAACTTAGCAAACTGCAGCCCCAA | 43 |

<3> Calculation of NTBS (Nexavar Treatment Benefit Score)

In order to evaluate whether a patient having susceptibility to sorafenib treatment can be selected using only the tumor tissues, we introduce a new parameter, i.e., NTBS (Nexavar Treatment Benefit Score), based on the expression levels of 7 marker genes in the tumor tissues. The NTBS value was calculated by the following formula:

$$NTBS=G_{VEGFR2}+G_{PDGFR\beta}+G_{c\text{-}KIT}+G_{c\text{-}RAF}+G_{EGFR}+G_{mTOR}+G_{FGFR1}$$

In the above formula, $G_{VEGFR2}$, $G_{PDGFR\beta}$, $G_{c\text{-}KIT}$, $G_{c\text{-}RAF}$, $G_{EGFR}$, $G_{mTOR}$, and $G_{FGFR1}$ refer to the mRNA expression levels ($2^{-\Delta CT}$) of the corresponding marker genes in the tumor tissues, respectively.

<4> Statistical Analysis

Statistical analyses in this study were carried out with the open source statistical programming environment R. $2^{-\Delta CT}$ values of each gene were shown in box and whisker plot and the difference between tumor and non-tumor tissues was evaluated for significance using Student's t-test. The relationship of gene expression with clinicopathologic variables was evaluated using $\chi 2$ and Fisher's exact tests. Up-regulated, unchanged, or down-regulated gene expression was evaluated using the fold difference of $2^{-\Delta CT}$ values between the tumors and the surrounding non-tumor tissues. Hierarchical clustering analyses of the T/N ratios (tumor/non-tumor) of $2^{-\Delta CT}$ values were performed for patient stratification.

2. Test Results (1) Frequency of mRNA Over-Expressions of the Marker Genes Associated with the Efficacy of Sorafenib In many kinds of cancer, the expressions of marker genes have been shown to be aberrantly regulated. The present inventors therefore investigated mRNA over-expressions for 4 marker genes (i.e., VEGFR2, PDGFRβ, c-KIT and c-RAF, which are known as genes associated with the efficacy of sorafenib) in 130 HCC and matched non-tumor tissues. The results are shown in FIG. 1. We considered at least twofold higher expression level ($2^{-\Delta CT}$) of each marker gene in tumor tissues than that in non-tumor tissues as over-expression thereof.

As shown in FIG. 1, 80.0% of the patients showed over-expression of at least one marker gene among the 4 marker genes. 21.54% of the patients showed over-expression of only one marker gene; 23.1% of the patients showed over-expression of two marker genes; 18.5% of the patients showed over-expression of three marker genes; and 16.9% of the patients showed over-expression of all the four marker genes. The results thereof suggest that the efficacy of sorafenib cannot be determined based on only over-expressions of said marker genes that are previously known as genes associated with the efficacy of sorafenib. Therefore, the present inventors performed analyses on expressions of various marker genes in addition to said marker genes (VEGFR2, PDGFRβ, c-KIT, c-RAF); and hierarchical clustering analyses thereof. As a result thereof, we confirmed that the additional 3 marker genes (EGFR, mTOR, FGFR1) as well as said marker genes (VEGFR2, PDGFRβ, c-KIT, c-RAF) need to be analyzed for clustering the patients showing different efficacy and safety profiles to sorafenib treatment (data not shown).

(2) Characterization of 7 Marker Gene Expressions

The expression levels ($2^{-\Delta CT}$) of 7 marker genes were analyzed in non-tumor tissues (NT) and tumor tissues (T) according to the Box-Whisker plot method. The expression levels of the marker genes at each BCLC stage (A: Early, B: intermediate, C: Advanced) were also analyzed in non-tumor tissues and tumor tissues (T). The difference of each marker gene expression between in tumor and in non-tumor tissues was evaluated for significance using Student's t-test and P values of $<0.05$ were considered statistically significant. The results thereof are shown in FIG. 2 In the FIG. 2, A to G respectively show the expression levels of VEGFR2 (A); PDGFRβ (B); c-KIT (C); c-RAF (D); EGFR (E); mTOR (F); and FGFR1 (G).

In case of VEGFR2 (FIG. 2A), the expression was up-regulated in all patients' tumor tissues compared to non-tumor tissues, but the difference thereof was statistically insignificant. However, the expression level was significantly higher in BCLC stage A patients' tumor tissues. The expression levels were also higher in BCLC stage B and C patients' tumor tissues, but each difference thereof was statistically insignificant.

In case of PDGFRβ (FIG. 2B), the expression was significantly higher in all patients' tumor tissues, as well as all BCLC stage A, B and C patients' tumor tissues, compared to non-tumor tissues.

In case of c-KIT (FIG. 2C), the expression was significantly higher in all patients' tumor tissues, as well as BCLC stage A and B patients' tumor tissues, in comparison to non-tumor tissues. The expression level was higher in BCLC stage C patients' tumor tissues compared to non-tumor tissues, but the difference thereof was statistically insignificant.

In case of c-RAF (FIG. 2D), the expression was significantly higher in all patients' tumor tissues, as well as all BCLC stage A, B and C patients' tumor tissues, compared to non-tumor tissues.

In case of EGFR (FIG. 2E), the expression level was significantly higher in all patients' tumor tissues compared to non-tumor tissues. However, the expression level was significantly higher only in BCLC stage A patients' tumor tissues. The expression level was also higher in BCLC stage B patients' tumor tissues, but the difference thereof was statistically insignificant. The expression level was even lower in BCLC stage C patients' tumor tissues, but the difference thereof was also statistically insignificant.

In case of mTOR (FIG. 2F), the expression was significantly higher in all patients' tumor tissues, as well as all BCLC stage A, B and C patients' tumor tissues, compared to non-tumor tissues.

In case of FGFR1 (FIG. 2G), the expression was even lower in all patients' tumor tissues, as well as all BCLC stage A, B and C patients' tumor tissues, compared to non-tumor tissues, but the differences thereof were statistically insignificant.

(3) Characterization of the Frequency of 7 Marker Gene Expressions

The present inventors measured the expression levels of 7 marker genes in the tumor tissues and the surrounding non-tumor tissues derived from 130 HCC patients and then investigated the frequency of over-expression in tumor tissues compared to non-tumor tissues. The results thereof are shown in FIG. 3. In FIG. 3, the red color shows the patients having at least twofold higher expression in tumor tissues compared to non-tumor tissues; the green color shows the patients having at least twofold lower expression in tumor tissues compared to non-tumor tissues; the black color shows the patients having expression higher or lower less than two times in tumor tissues compared to non-tumor tissues, i.e., the patients who were considered to have no significant difference. EGFR mRNA levels were up-regulated in 35.4% of the tumors and unchanged in 47.7% of the tumors. VEGFR2 was up-regulated, unchanged, and down-regulated in 42.3%, 39.2%, and 18.5% of the tumors, respectively. PDGFRβ was up-regulated in tumors at a high rate (61.5%). While patients with unchanged and down-regulated expression of FGFR1 were 40% and 35.4%, respectively, only 24.6% of the patients showed up-regulation of FGFR1 in the tumors. mTOR was found to be up-regulated in half of the tumors.

In addition, we measured the expression levels of 7 marker genes in the tumor tissues and the surrounding non-tumor tissues derived from 130 HCC patients and then examined the frequency of over-expression in tumor tissues compared to non-tumor tissues, according to the BCLC stages. The results thereof are shown in FIG. 4. In FIG. 4, the red color shows the patients having at least twofold higher expression in tumor tissues compared to non-tumor tissues; the green color shows the patients having at least twofold lower expression in tumor tissues compared to non-tumor tissues; the black color shows the patients having expression higher or lower less than two times in tumor tissues compared to non-tumor tissues, i.e., the patients who were considered to have no significant difference. Up-regulation of EGFR was observed in 41.9% of the tumors at BCLC stage A but the proportion decreased by 17.6% at later stages and down-regulation of EGFR was prominently found in advanced stage tumors (35.3%). The stage association of VEGFR2 up-regulation was similar to that of EGFR. Up-regulation of PDGFRβ was observed in 66.2%, 51.3%, and 64.7% of the tumors at BCLC stages A, B, and C, respectively. FGFR1 levels were up-regulated in about 20% of the tumors irrespective of stage. mTOR was up-regulated in about half of the tumors in all the stages.

(4) Association of Clinical Characteristics with Marker Gene Expression

To gain further insight into the gene expression of biomarkers in HCC, the relationships between mRNA levels of the genes and clinicopathologic features were investigated. High mRNA expression of EGFR was correlated with the BCLC stage (P=0.049, Tables 3 and 4). The degree of tumor differentiation (Edmondson grade) was significantly associated with expression of both EGFR and VEGFR2 (P=0.003 and 0.004, respectively), which showed that well-differentiated HCC tended to express EGFR and VEGFR2 at high levels. EGFR was significantly over-expressed in single tumors (P=0.001).

TABLE 3

| | | EGFR | | | VEGFR2 | | | PDGFRβ | | |
|---|---|---|---|---|---|---|---|---|---|---|
| | | Low (n = 22) | High (n = 46) | p Value | Low (n = 24) | High (n = 55) | p Value | Low (n = 15) | High (n = 80) | p Value |
| Age | <55 years | 15 | 24 | 0.324 | 18 | 30 | 0.144 | 9 | 51 | 0.988 |
| | ≥55 years | 7 | 22 | | 6 | 25 | | 6 | 29 | |
| Gender | Male | 17 | 33 | 0.849 | 16 | 40 | 0.783 | 10 | 60 | 0.53 |
| | Female | 5 | 13 | | 8 | 15 | | 5 | 20 | |
| HBV | Absent | 4 | 14 | 0.437 | 3 | 18 | 0.111 | 2 | 21 | 0.348 |
| | Present | 18 | 32 | | 21 | 37 | | 13 | 59 | |
| HCV | Absent | 19 | 41 | 0.707 | 22 | 47 | 0.715 | 14 | 72 | 1 |
| | Present | 3 | 5 | | 2 | 8 | | 1 | 8 | |
| Liver cirrhosis | Absent | 12 | 26 | 0.991 | 14 | 33 | 0.985 | 7 | 46 | 0.587 |
| | Present | 10 | 19 | | 10 | 21 | | 8 | 33 | |
| Tumor stage | I-II | 15 | 40 | 0.098 | 18 | 43 | 0.985 | 14 | 64 | 0.293 |
| | III-IV | 7 | 6 | | 6 | 12 | | 1 | 16 | |
| Child-Pugh class | A | 22 | 44 | 1 | 22 | 53 | 0.581 | 15 | 77 | 1 |
| | B | 0 | 2 | | 2 | 2 | | 0 | 3 | |
| BCLC stage | A | 10 | 31 | 0.049 | 14 | 34 | 0.614 | 10 | 49 | 0.844 |
| | B | 6 | 12 | | 6 | 16 | | 4 | 20 | |
| | C | 6 | 3 | | 4 | 5 | | 1 | 11 | |
| AFP level | <100 ng/ml | 10 | 29 | 0.267 | 11 | 39 | 0.061 | 9 | 49 | 0.844 |
| | ≥100 ng/ml | 12 | 17 | | 13 | 16 | | 6 | 31 | |
| Vascular invasion | Absent | 7 | 22 | 0.324 | 7 | 29 | 0.091 | 8 | 34 | 0.623 |
| | Present | 15 | 24 | | 17 | 26 | | 7 | 46 | |
| Tumor number | Single | 11 | 41 | 0.001 | 18 | 47 | 0.338 | 13 | 67 | 1 |
| | Multiple | 11 | 5 | | 6 | 8 | | 2 | 13 | |
| Tumor size | ≤5 cm | 15 | 35 | 0.691 | 17 | 40 | 0.92 | 11 | 61 | 0.754 |
| | >5 cm | 7 | 11 | | 7 | 15 | | 4 | 19 | |
| Edmondson grade | I | 0 | 14 | 0.003 | 0 | 15 | 0.004 | 2 | 12 | 1 |
| | II-III | 22 | 32 | | 24 | 40 | | 13 | 68 | |

TABLE 4

| | | FGFR1 | | | mTOR | | |
|---|---|---|---|---|---|---|---|
| | | Low (n = 46) | High (n = 32) | p Value | Low (n = 12) | High (n = 65) | p Value |
| Age | <55 years | 26 | 24 | 0.152 | 8 | 41 | 1 |
| | ≥55 years | 20 | 8 | | 4 | 24 | |
| Gender | Male | 35 | 21 | 0.451 | 9 | 44 | 0.744 |
| | Female | 11 | 11 | | 3 | 21 | |
| HBV | Absent | 7 | 3 | 0.513 | 0 | 13 | 0.201 |
| | Present | 39 | 29 | | 12 | 52 | |
| HCV | Absent | 41 | 31 | 0.392 | 12 | 60 | 1 |
| | Present | 5 | 1 | | 0 | 5 | |
| Liver cirrhosis | Absent | 21 | 18 | 0.403 | 5 | 34 | 0.717 |
| | Present | 25 | 13 | | 7 | 31 | |
| Tumor stage | I-II | 40 | 26 | 0.536 | 12 | 50 | 0.109 |
| | III-IV | 6 | 6 | | 0 | 15 | |
| Child-Pugh class | A | 45 | 32 | 1 | 12 | 64 | 1 |
| | B | 1 | 0 | | 0 | 1 | |
| BCLC stage | A | 27 | 20 | 0.7 | 8 | 35 | 0.456 |
| | B | 15 | 8 | | 4 | 20 | |
| | C | 4 | 4 | | 0 | 10 | |
| AFP level | <100 ng/ml | 24 | 21 | 0.342 | 7 | 39 | 1 |
| | ≥100 ng/ml | 22 | 11 | | 5 | 26 | |
| Vascular invasion | Absent | 17 | 14 | 0.713 | 6 | 28 | 0.899 |
| | Present | 29 | 18 | | 6 | 37 | |
| Tumor number | Single | 38 | 26 | 0.884 | 11 | 52 | 0.684 |
| | Multiple | 8 | 6 | | 1 | 13 | |
| Tumor size | ≤5 cm | 32 | 24 | 0.788 | 9 | 46 | 1 |
| | >5 cm | 14 | 8 | | 3 | 19 | |
| Edmondson grade | I | 4 | 6 | 0.302 | 1 | 12 | 0.679 |
| | II-III | 42 | 26 | | 11 | 53 | |

(5) Hierarchical Clustering Analysis

The present inventors carried out a hierarchical clustering analysis for clustering the patients. The results thereof are shown in FIG. 5. The expression levels of each marker gene ($2^{-\Delta CT}$) were calculated as a ratio of the expression level of the marker gene in tumor tissues to the expression level of the marker gene in non-tumor tissues (i.e., tumor/non-tumor). In FIG. 5, the red color shows the patients having at least fourfold higher expression in tumor tissues compared to non-tumor tissues; the dark red color shows the patients having at least twofold higher expression in tumor tissues compared to non-tumor tissues; the black color shows the patients having expression higher or lower less than two times in tumor tissues compared to non-tumor tissues, i.e., the patients having no significant difference between the expression levels; the dark green color shows the patients having at least twofold lower expression in tumor tissues compared to non-tumor tissues; and the green color shows the patients having at least fourfold lower expression in tumor tissues compared to non-tumor tissues. In the BCLC stage which means a hepatocellular carcinoma stage, A shows an early-HCC (blue color); B shows an intermediate-HCC (green color); and C shows an advanced-HCC (red color). In FIG. 5, the row means individual target molecules; and the column means the 130 individual patents. The patients were primarily categorized according to the BCLC stages and then clustered according to the expression ratios (tumor/non-tumor) of the target molecules.

As shown in FIG. 5, it can be seen that the 130 patients can be classified into a certain cluster according to the BCLC stages and the marker genes. That is, the patients over-expressing all the 7 marker genes in the BCLC stage A can be classified into the 'Patient Group aI'; the patients over-expressing the 5 marker genes (VEGFR2, PDGFRβ, c-KIT, c-RAF and FGFR1) but down-expressing the 2 genes (EGFR and mTOR) in the BCLC stage A can be classified into the 'Patient Group aII'; and the patients down-expressing all the 7 marker genes in the BCLC stage A can be classified into the 'Patient Group aIII'. Patients of the BCLC stages B and C can be classified according to the same manners as in the BCLC stage A. Therefore, through the hierarchical cluster analysis, it can be expected that patients showing different biomarker expressions will result in different efficacy and safety profiles to a molecular targeted agent, e.g., sorafenib.

(6) Susceptibility Assay in Sorafenib-Administered Patients

In the samples derived from 23 sorafenib-administered patients, we analyzed the relationship between the 7 marker gene expression patterns and the sorafenib efficacies. From the hierarchical clustering analysis results of FIG. 5, clustering without primary classification according to BCLC stages was performed according to expression ratio (tumor/non-tumor) of the target molecules; and then the 23 sorafenib-administered patients (i to xxiii) were correspondingly arranged thereto (FIG. 6). Among the 23 sorafenib-administered patients, only the patients "viii, x, xi" were susceptible to the sorafenib treatment, i.e. showed partial response according to RECIST (Response Evaluation Criteria in Solid Tumors) which is defined in Llovet J M, et al. (2008) Sorafenib in advanced hepatocellular carcinoma. *N Engl J Med* 359: 378-390. The remaining 20 patients were not susceptible to the sorafenib treatment.

When the 23 sorafenib-administered patients' susceptible/unsusceptible responses were correspondingly arranged to the hierarchical clustering analysis results, it can be seen that the patients down-expressing mRNA of the FGFR1 gene (the gene of SEQ ID NO: 1) (i.e., patients i to vii, ix, and xii to xxiii) in the tumor tissues were not susceptible to the sorafenib treatment. Therefore, if the expression level of mRNA of the FGFR1 gene is higher in the HCC tumor tissues than the expression level thereof in the normal tissues [i.e., when the T/N (tumor/non-tumor) ratio of the FGFR1 gene is more than 2], the patient can be classified to a patient having low resistance to sorafenib treatment, i.e., a patient having high susceptibility to sorafenib treatment. Since there is no report regarding the relationship between sorafenib and the FGFR1 gene, these results are very surprising And also, the analyses on mRNA expression of VEGFR2 (the gene of SEQ ID NO: 2), PDGFRβ (the gene of SEQ ID NO: 3), c-KIT (the gene of SEQ ID NO: 4), and c-RAF (the gene of SEQ ID NO: 5) which are known as target genes of sorafenib; and/or EGFR (the gene of SEQ ID NO: 6) and mTOR (the gene of SEQ ID NO: 7) which are known as resistant genes to sorafenib, in combination with mRNA expression of the FGFR1 gene, make it possible to more efficiently select the patients having susceptibility to sorafenib treatment. For example, if (1) the T/N ratio of the FGFR1 gene is more than 2; (2) the T/N ratio(s) of one or more genes selected from the group consisting of VEGFR2, PDGFRβ, c-KIT, and c-RAF is (are) more than 2; and (3) the T/N ratio(s) of one or more genes selected from the group consisting of EGFR and mTOR is (are) less than 2, the patient can be classified to a patient having low resistance to sorafenib treatment, i.e., a patient having high susceptibility to sorafenib treatment.

From the results of FIG. 6, it can be also seen that PDGFRβ (the gene of SEQ ID NO: 3), c-KIT (the gene of SEQ ID NO: 4), EGFR (the gene of SEQ ID NO: 6), and mTOR (the gene of SEQ ID NO: 7) among them are more preferable as genes for analyzing in combination with the FGFR1 gene. Therefore, for example, if (1) the T/N ratio of the FGFR1 gene is more than 2; (2) the T/N ratios of PDGFRβ and c-KIT are more than 2; and (3) the T/N ratio of EGFR and mTOR is less than 2, the patient can be classified to a patient having low resistance to sorafenib treatment, i.e., a patient having high susceptibility to sorafenib treatment.

(7) Susceptibility Assay Based on NTBS Values in Sorafenib-Administered Patients The present inventors also evaluated whether a patient having susceptibility to sorafenib treatment can be selected using only the tumor tissues. We calculated the NTBS value based on the mRNA expression levels of 7 marker genes in each 23 sorafenib-administered patients' tumor tissues. The results thereof are shown in FIG. 7 (A) and Table 5 below.

TABLE 5

| HCC patients | NTBS |
|---|---|
| i | 0.001851 |
| ii | 0.001784 |
| iii | 0.029121 |
| iv | 0.002138 |
| v | 0.059301 |
| vi | 0.033066 |
| vii | 0.018625 |
| viii | 0.1735 |
| ix | 0.003082 |
| x | 0.11626 |
| xi | 0.1144 |
| xii | 0.027969 |
| xiii | −0.00073 |
| xiv | 0.047356 |
| xv | 0.07577 |
| xvi | 0.029827 |
| xvii | −0.00108 |
| xviii | 0.003726 |
| xix | 0.029899 |

TABLE 5-continued

| HCC patients | NTBS |
|---|---|
| xx | 0.00343 |
| xxi | 0.028935 |
| xxii | 0.027161 |
| xxiii | −0.00165 |

In FIG. 7 (A), S refers to the NTBS values obtained from the patients susceptible to the sorafenib treatment (i.e. patients viii, x, and xi); and R refers to the NTBS values obtained from the patients not susceptible to the sorafenib treatment (i.e. patients i to vii, ix, and xii to xxiii). The ROC (receiver operating characteristic) curve obtained from the NTBS values is shown in FIG. 7 (B). The threshold value calculated from the analysis of ROC curve was 0.0758. From the above results, it can be seen that a patient having susceptibility to sorafenib treatment can be selected using the parameter, i.e., NTBS. That is, if the NTBS value is more than the threshold value (i.e., 0.0758), preferably more than 0.1, the patient can be classified to a patient having susceptibility to sorafenib treatment.

The invention claimed is:

1. An analytical method for determining whether a hepatocellular carcinoma patient has susceptibility or resistance to sorafenib treatment, comprising (i') measuring mRNA expression levels of the genes of SEQ ID NOs: 1 to 7 in both the hepatocellular carcinoma tissues and normal tissues isolated from the body of the hepatocellular carcinoma patient by performing real-time reverse transcriptase-polymerase chain reaction with primer sets for amplifying the genes of SEQ ID NOs: 1 to 7, wherein the primer sets are: a forward primer comprising SEQ ID NO: 32 and a reverse primer comprising SEQ ID No: 33 for amplifying SEQ ID NO: 1, a forward primer comprising SEQ ID NO: 26 and a reverse primer comprising SEQ ID No: 27 for amplifying SEQ ID NO: 2, a forward primer comprising SEQ ID NO: 29 and a reverse primer comprising SEQ ID No: 30 for amplifying SEQ ID NO: 3, a forward primer comprising SEQ ID NO: 41 and a reverse primer comprising SEQ ID No: 42 for amplifying SEQ ID NO: 4, a forward primer comprising SEQ ID NO: 38 and a reverse primer comprising SEQ ID No: 39 for amplifying SEQ ID NO: 5, a forward primer comprising SEQ ID NO: 23 and a reverse primer comprising SEQ ID No: 24 for amplifying SEQ ID NO: 6, and a forward primer comprising SEQ ID NO: 35 and a reverse primer comprising SEQ ID No: 36 for amplifying SEQ ID NO: 7, (ii') measuring the ratio between the mRNA expression levels of the genes of SEQ ID NOs: 1 to 7 in the hepatocellular carcinoma tissues and the mRNA expression levels of the genes of SEQ ID NOs: 1 to 7 in the normal tissues, and (iii') determining whether the patient has susceptibility or resistance to sorafenib treatment, wherein if (1) each ratio of the mRNA expression levels of the genes of SEQ ID NOs: 1 to 5 in hepatocellular carcinoma tissues to the mRNA expression levels of the genes of SEQ ID NOs: 1 to 5 in normal tissues is more than 2; and (2) each ratio of the mRNA expression levels of the genes of SEQ ID NOs: 6 to 7 in hepatocellular carcinoma tissues to the mRNA expression levels of the genes of SEQ ID NOs: 6 to 7 in normal tissues is less than 2, the patient is determined as a patient having susceptibility to sorafenib treatment, and wherein if (1) each ratio of mRNA expression levels of the genes of SEQ ID NOs: 1 to 5 in hepatocellular carcinoma tissues to the mRNA expression levels of the genes of SEQ ID NOs: 1 to 5 in normal tissues is less than 2; and (2) each ratio of the mRNA expression levels of the genes of SEQ ID NOs: 6 to 7 in hepatocellular carcinoma tissues to the mRNA expression levels of the genes of SEQ ID NOs: 6 to 7 in normal tissues is more than 2, the patient is determined as a patient having resistance to sorafenib treatment.

2. An analytical method for determining whether a hepatocellular carcinoma patient has susceptibility or resistance to sorafenib treatment, comprising (i''') measuring mRNA expression levels of the genes of SEQ ID NOs: 1 to 7 in the hepatocellular carcinoma tissues isolated from the body of the hepatocellular carcinoma patient by performing real-time reverse transcriptase-polymerase chain reaction with primer sets for amplifying the genes of SEQ ID NOs: 1 to 7, and then calculating the respective $2^{-\Delta CT}$ level of the genes of SEQ ID NOs: 1 to 7, wherein the primer sets are a forward primer comprising SEQ ID NO: 32 and a reverse primer comprising SEQ ID No: 33 for amplifying SEQ ID NO: 1, a forward primer comprising SEQ ID NO: 26 and a reverse primer comprising SEQ ID No: 27 for amplifying SEQ ID NO: 2, a forward primer comprising SEQ ID NO: 29 and a reverse primer comprising SEQ ID No: 30 for amplifying SEQ ID NO: 3, a forward primer comprising SEQ ID NO: 41 and a reverse primer comprising SEQ ID No: 42 for amplifying SEQ ID NO: 4, a forward primer comprising SEQ ID NO: 38 and a reverse primer comprising SEQ ID No: 39 for amplifying SEQ ID NO: 5, a forward primer comprising SEQ ID NO: 23 and a reverse primer comprising SEQ ID No: 24 for amplifying SEQ ID NO: 6, and a forward primer comprising SEQ ID NO: 35 and a reverse primer comprising SEQ ID No: 36 for amplifying SEQ ID NO: 7, (ii''') calculating the sum of respective $2^{-\Delta CT}$ level of the genes of SEQ ID NOs: 1 to 7, and (iii''') determining whether the patient has susceptibility or resistance to sorafenib treatment, wherein the sum is more than 0.0758, the patient is determined as a patient having susceptibility to sorafenib treatment, and wherein the sum is less than 0.0758, the patient is determined as a patient having resistance to sorafenib treatment.

* * * * *